United States Patent
Bouwstra et al.

(10) Patent No.: US 9,034,914 B2
(45) Date of Patent: May 19, 2015

(54) PHARMACEUTICAL COMPOSITION COMPRISING ROTIGOTINE SALTS (ACID OR NA), ESPECIALLY FOR IONTOPHORESIS

(71) Applicant: UCB Pharma GmbH, Monheim (DE)

(72) Inventors: Johanna Aaltje Bouwstra, WB Barendrecht (NL); Oliver Ackaert, Essen (BE); Jacob Eikelenboom, MZ Haarlem (NL); Hans-Michael Wolff, Monheim (DE)

(73) Assignee: UCB PHARMA GMBH, Monheim (DE)

( * ) Notice: Subject to any disclaimer, the term of this patent is extended or adjusted under 35 U.S.C. 154(b) by 0 days.

(21) Appl. No.: 14/230,177

(22) Filed: Mar. 31, 2014

(65) Prior Publication Data

US 2014/0243386 A1 Aug. 28, 2014

Related U.S. Application Data

(62) Division of application No. 13/379,333, filed as application No. PCT/EP2010/003796 on Jun. 24, 2010, now Pat. No. 8,754,120.

(30) Foreign Application Priority Data

Jun. 26, 2009 (EP) .................... 09008401

(51) Int. Cl.
*A61K 31/381* (2006.01)
*C07D 333/20* (2006.01)
*A61K 9/00* (2006.01)
*A61N 1/30* (2006.01)

(52) U.S. Cl.
CPC ............. *A61K 31/381* (2013.01); *A61K 9/0009* (2013.01); *C07D 333/20* (2013.01); *A61N 1/30* (2013.01)

(58) Field of Classification Search
USPC ...................... 514/438; 549/74, 75
See application file for complete search history.

(56) References Cited

U.S. PATENT DOCUMENTS

| | | | |
|---|---|---|---|
| 5,177,112 A | 1/1993 | Horn | |
| 5,382,596 A | 1/1995 | Sleevi et al. | |
| 6,372,920 B1 | 4/2002 | Minaskanian et al. | |
| 6,884,434 B1 | 4/2005 | Muller et al. | |
| 7,217,705 B2 | 5/2007 | Benavides et al. | |
| 7,309,497 B2 | 12/2007 | Rimpler et al. | |
| 7,413,747 B2 | 8/2008 | Mueller et al. | |
| 7,632,859 B2 | 12/2009 | Li et al. | |
| 7,683,040 B2 | 3/2010 | Kramer | |
| 7,872,041 B2 | 1/2011 | Scheller | |
| 8,211,462 B2 | 7/2012 | Breitenbach et al. | |
| 8,232,414 B2 | 7/2012 | Wolff et al. | |
| 8,246,979 B2 | 8/2012 | Schacht et al. | |
| 8,246,980 B2 | 8/2012 | Schacht et al. | |
| 8,283,376 B2 | 10/2012 | Scheller et al. | |
| 8,545,872 B2 | 10/2013 | Breitenbach | |
| 8,592,477 B2 | 11/2013 | Wolff et al. | |
| 8,604,076 B2 | 12/2013 | Rimpler et al. | |
| 8,609,641 B2 | 12/2013 | Scheller et al. | |
| 8,617,591 B2 | 12/2013 | Schacht et al. | |
| 2003/0026830 A1 | 2/2003 | Lauterback et al. | |
| 2003/0027793 A1 | 2/2003 | Lauterback et al. | |
| 2003/0166709 A1 | 9/2003 | Rimpler et al. | |
| 2004/0034083 A1 | 2/2004 | Stephenson et al. | |
| 2004/0048779 A1 | 3/2004 | Schollmayer | |
| 2004/0081683 A1 | 4/2004 | Schacht et al. | |
| 2004/0116537 A1 | 6/2004 | Li et al. | |
| 2004/0137045 A1 | 7/2004 | Breitenbach et al. | |
| 2004/0209861 A1 | 10/2004 | Benavides et al. | |
| 2005/0033065 A1 | 2/2005 | Mueller et al. | |
| 2005/0079206 A1 | 4/2005 | Schacht et al. | |
| 2005/0175678 A1 | 8/2005 | Breitenbach | |
| 2005/0197385 A1 | 9/2005 | Scheller et al. | |
| 2005/0260254 A1 | 11/2005 | Breitenbach et al. | |
| 2006/0216336 A1 | 9/2006 | Wolff | |
| 2006/0263419 A1 | 11/2006 | Wolff | |
| 2007/0072917 A1 | 3/2007 | Scheller et al. | |
| 2007/0093546 A1 | 4/2007 | Scheller et al. | |
| 2007/0191308 A1 | 8/2007 | Kramer | |
| 2007/0191470 A1 | 8/2007 | Scheller | |
| 2007/0197480 A1 | 8/2007 | Scheller et al. | |
| 2008/0008748 A1 | 1/2008 | Beyreuther et al. | |
| 2008/0138389 A1 | 6/2008 | Muller et al. | |
| 2008/0146622 A1 | 6/2008 | Scheller | |
| 2008/0274061 A1 | 11/2008 | Schollmayer et al. | |

(Continued)

FOREIGN PATENT DOCUMENTS

| | | |
|---|---|---|
| CA | 2483120 A1 | 11/2003 |
| CA | 2547645 A1 | 7/2005 |

(Continued)

OTHER PUBLICATIONS

Danhof, M., et al. (1998) "An integrated pharmacokinetic—pharmacodynamics approach to optimization of R-apomorphine delivery in parkinson's disease" Advanced Drug Delivery Reviews, 33:253-263.

(Continued)

*Primary Examiner* — Kristin Vajda
(74) *Attorney, Agent, or Firm* — Harness, Dickey & Pierce, P.L.C.

(57) ABSTRACT

The present invention relates to new salts of 6-(propyl-(2-thiophen-2-ylethyl)amino)tetralin-1-ol(rotigotine), their use as a medicament, for example for the treatment of CNS disorders like Parkinson Disease, RLS, fibromyalgia and/or depression, in particular through electromotive administration. The present invention relates to pharmaceutical formulations suitable for iontophoresis that provide enhanced iontophoretic delivery of rotigotine to at least one target tissue. The formulations are further characterized by good to excellent solubility of the salts in aqueous solutions.

12 Claims, 18 Drawing Sheets

(56) References Cited

U.S. PATENT DOCUMENTS

| | | |
|---|---|---|
| 2009/0143460 A1 | 6/2009 | Wolff et al. |
| 2010/0311806 A1 | 12/2010 | Wolff et al. |
| 2011/0104281 A1 | 5/2011 | Beyreuther et al. |
| 2011/0165247 A1 | 7/2011 | Breitenbach |
| 2012/0101146 A1 | 4/2012 | Bouwstra et al. |
| 2012/0215185 A1 | 8/2012 | Schacht et al. |
| 2012/0322845 A1 | 12/2012 | Wolff et al. |
| 2013/0251791 A1 | 9/2013 | Seth et al. |
| 2014/0051768 A1 | 2/2014 | Scheller et al. |

FOREIGN PATENT DOCUMENTS

| | | |
|---|---|---|
| WO | WO-94/07468 A1 | 4/1994 |
| WO | WO-99/49852 A1 | 10/1999 |
| WO | WO-02/15903 A2 | 2/2002 |
| WO | WO-02/089777 A1 | 11/2002 |
| WO | WO-03/092677 A1 | 11/2003 |
| WO | WO-2004/050083 A1 | 6/2004 |
| WO | WO-2005/009424 A1 | 2/2005 |
| WO | WO-2005/063237 A1 | 7/2005 |
| WO | WO-2005/092331 A1 | 10/2005 |
| WO | WO-2009/063171 A1 | 5/2009 |

OTHER PUBLICATIONS

International Preliminary Report on Patentability and Written Opinion for PCT/EP2010/003796 dated Jan. 4, 2012.

International Search Report and Written Opinion for PCT/EP2010/003796 dated Feb. 8, 2011.

Luzardo-Alvarez, A., et al. (2001) "Iontophoretic delivery of ropinirole hydrochorlide: effect of current density and vehicle formulation" Pharmaceutical Research, vol. 18, No. 12, pp. 1713-1720.

Nair, V., et al. (1999) "Transdermal iontophoresis. Part I: basic principles and considerations" Methods Find Exp Clin Pharmacol, 21(2):139-151.

Nugroho, A.K., et al. (2004) "Transdermal iontophoresis of rotigotine across human stratum corneum in vitro: influence of pH and NaCl concentration" Pharmaceutical Research, vol. 21, No. 5, pp. 844-850.

Nugroho, A.K., et al. (2004) "Transdermal iontophoresis of rotigotine: influence of concentration, temperature and current density in human skin in vitro" Journal of Controlled Release 96:159-167.

Nugroho, et al. (2005) "Transdermal iontophoresis of the dopamine agonist 5-OH-DPAT in human skin in vitro" Journal of Controlled Release, 103, 393-403.

Office Action dated Oct. 1, 2010 issued in U.S. Appl. No. 10/429,283.

Office Action dated Dec. 10, 2008 issued in U.S. Appl. No. 10/565,713.

Office Action dated Sep. 10, 2008 issued in U.S. Appl. No. 10/429,283.

Office Action dated Jun. 11, 2012 issued in U.S. Appl. No. 12/744,989.

Office Action dated Nov. 12, 2013 issued in U.S. Appl. No. 13/379,333.

Office Action dated Jan. 15, 2014 issued in U.S. Appl. No. 10/429,283.

Office Action dated Aug. 16, 2010 issued in U.S. Appl. No. 11/239,701.

Office Action dated Mar. 21, 2013 issued in U.S. Appl. No. 13/379,333.

Office Action dated Dec. 23, 2009 issued in U.S. Appl. No. 10/429,283.

Office Action dated Feb. 3, 2012 issued in U.S. Appl. No. 10/429,283.

Office Action dated May 3, 2013 issued in U.S. Appl. No. 10/429,283.

Office Action dated Mar. 30, 2009 issued in U.S. Appl. No. 10/429,283.

Office Action dated Dec. 31, 2012 issued in U.S. Appl. No. 13/379,333.

Office Action dated May 4, 2011 issued in U.S. Appl. No. 10/429,283.

Office Action dated Aug. 5, 2009 issued in U.S. Appl. No. 10/593,964.

Van der Geest, R., et al. (1997) "Iontophoretic delivery of apomorphine I: in vitro optimization and validation" Pharmaceutical Research, vol. 14, No. 12, pp. 1798-1803.

Van der Weide, et al. (1988) "The enantiomers of the D-2 dopamine receptor agonist N-0437 discriminate between pre- and postsynaptic dopamine receptors." Eur J Pharmacol 146:319-326.

Hashida Mitsuru (1995), "Keikotoyoseizai no sekki to hyouka", *Kabushikigaisha Yakugyoujihousha*, pp. 76-77—partial English translation ($2^{nd}$ paragraph on p. 76).

Matsumoto Mitsuo (1989), "Yakuzaigaku manual—Pharmaceutical Sciences", *Nanzando*, p. 29—partial English translation ($1^{st}$ and $2^{nd}$ rows of the table on p. 29).

Wermuth, G.C. (1999), "Souyakukagaku—The Practice of Medicinal Chemistry", *Technomics*, vol. 2: pp. 347-365—partial English translation ($2^{nd}$ and $3^{rd}$ paragraphs on p. 348).

Figure 1: EXEMPLARILY DESIGN OF THE IONTOPHORESIS CELL
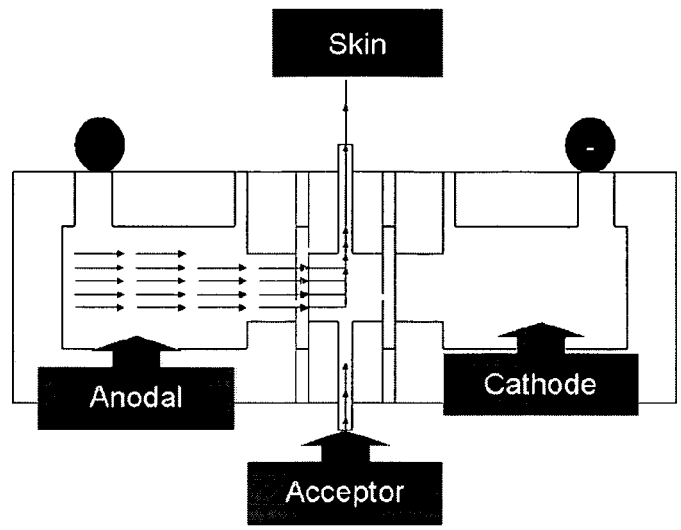
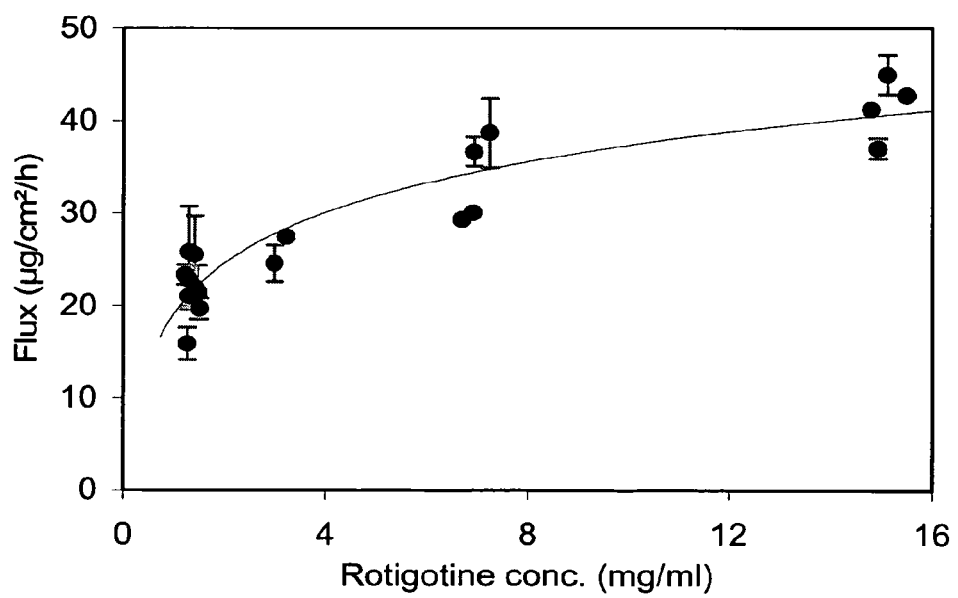
Figure 2: iontophoretic steady state flux ± s.d. (n=1-4 cells) of rotigotine *versus* drug concentration. pH (donor) = 5.0. Other conditions: see text. The fitted line is from equation:
Flux = 7.94 × Ln(Ro. conc.) + 19.09

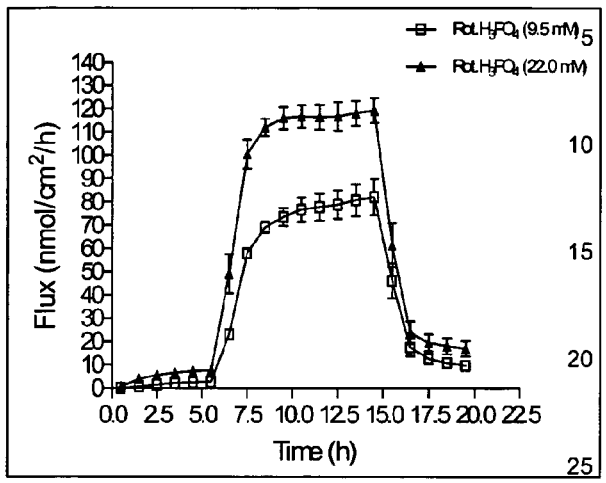

Figure 3: The iontophoretic flux time profile of Rotigotine.$H_3PO_4$ dissolved in citric buffer pH 5, containing 68 mM NaCl at 2 different concentrations, 9.5 mM (open square) and 22.0 mM (closed triangle). Data are presented as mean ± S.D. (n=3). Current density = 500 µA.cm$^{-2}$.

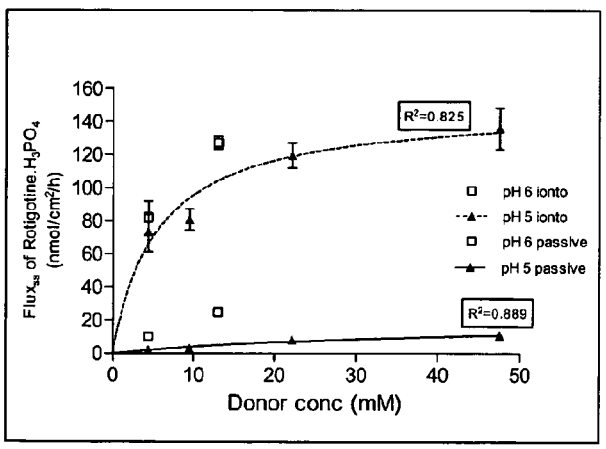

Figure 4: The correlation of the Flux$_{ss}$ during the passive phase (no current) and the iontophoretic phase (current density = 500 µA.cm$^{-2}$) versus the donor concentration at a donor pH 5 (closed triangle) and pH 6 (open square). The line of correlation of the passive Flux$_{ss}$ vs donor concentration is full and the line of correlation of the iontophoretic Flux$_{ss}$ vs donor concentration is intermittent. Data are presented as mean ± S.D. (n=3).

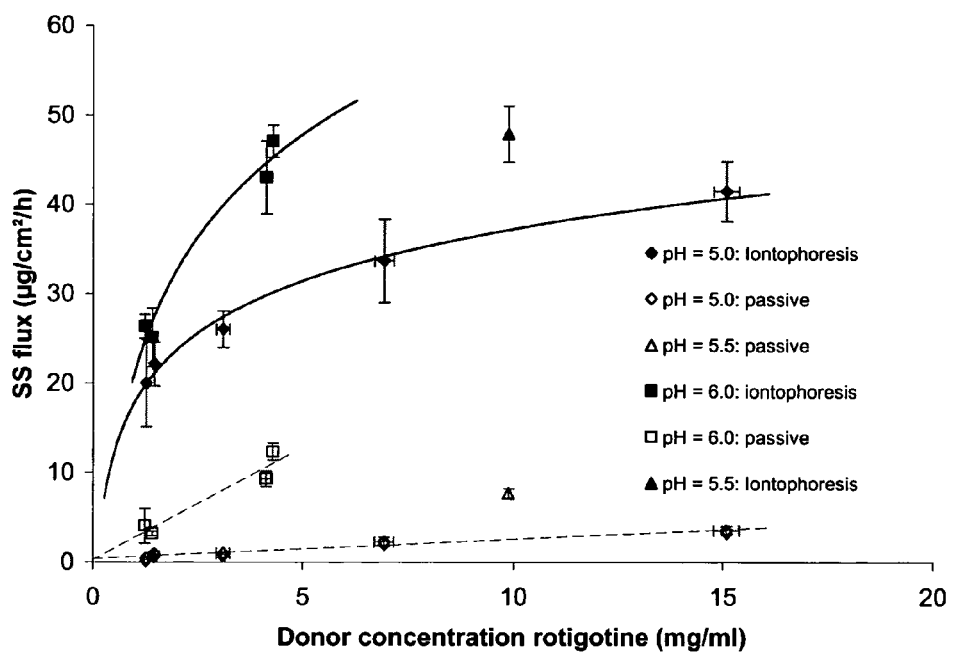
Figure 5 Combined impact of donor solution pH and drug concentration on passive and iontophoresis transdermal steady state flux of rotigotine. The fitted line are calculated from equations: Flux = 7.94 × Ln(Ro. conc.) + 19.09 (pH=5.0) and Flux = 14,94 × Ln(Ro.conc.) + 21,65 (pH = 6.0).

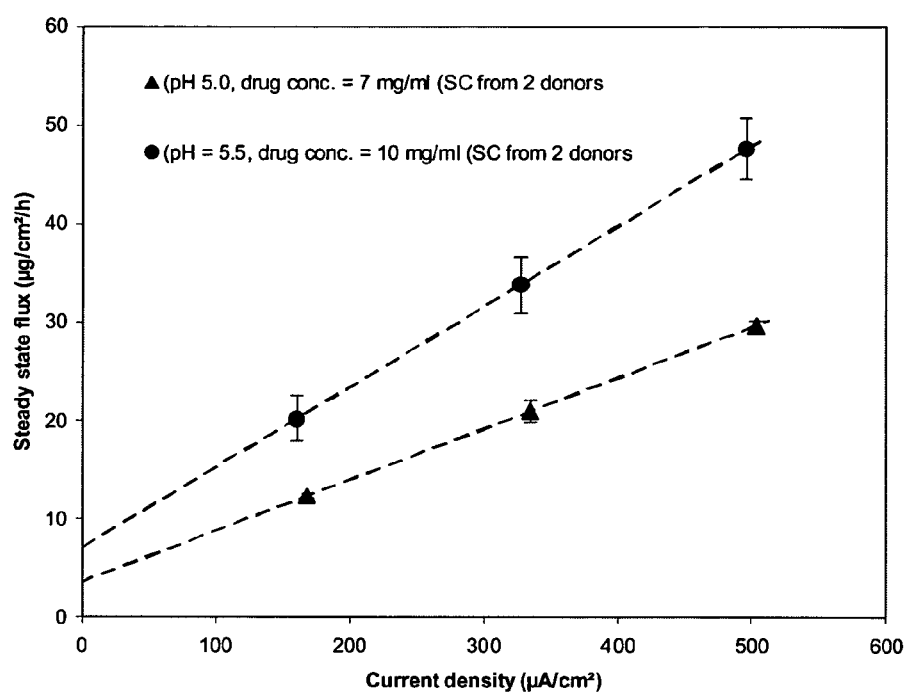
Figure 6: impact of current density on transdermal steady state drug flux from donor solutions containing 7.0 mg/ml/pH=5.0 (protocol a) or 9.9 mg/ml/pH=5.5 (protocol b) (SC: stratum corneum)

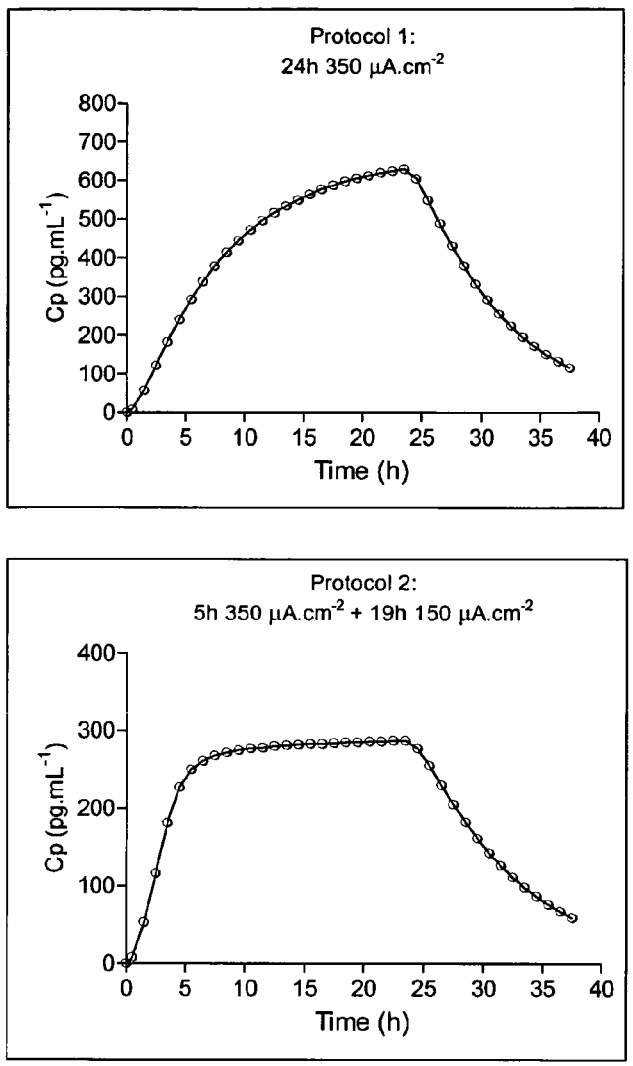
Figure 7: Population prediction of the simulations of iontophoretic delivery of rotigotine.$H_3PO_4$ (47 mM) using different protocols: Protocol 1: 24h 350 $\mu A.cm^{-2}$; Protocol 2: 5h 350 $\mu A.cm^{-2}$ + 19h 150 $\mu A.cm^{-2}$. The filled circles are the geometric mean of the population prediction of the plasma concentration (Cp).

PHARMACEUTICAL COMPOSITION COMPRISING ROTIGOTINE SALTS (ACID OR NA), ESPECIALLY FOR IONTOPHORESIS

CROSS-REFERENCE TO RELATED APPLICATIONS

This present application is a divisional application of U.S. patent application Ser. No. 13/379,333, filed 19 Dec. 2011, which is a national stage application of International Application No. PCT/EP2010/003796 filed on 24 Jun. 2010, which claims priority to EP Application No. 09008401.3 filed on 26 Jun. 2009. Each of the above-referenced patent applications is incorporated herein by reference in its entirety.

FIELD OF THE INVENTION

The present invention relates to new salts of 6-(propyl-(2-thiophen-2-ylethyl)amino)tetralin-1-ol(rotigotine), their use as a medicament, for example for the treatment of Parkinson Disease, RLS, fibromyalgia and/or depression, in particular through electromotive administration.

In another aspect the invention relates to a device, composition and method for improved electrotransport delivery of rotigotine and/or its salts respectively.

The present invention provides pharmaceutical formulations suitable for iontophoresis that provide enhanced iontophoretic delivery of rotigotine to at least one target tissue. The formulations are further characterized by good to excellent solubility of the salts in aqueous solutions. The present invention also provides methods of administering rotigotine in at least one target tissue of and/or treating one of the diseases mentioned above in a patient by iontophoretically delivering a formulation of the invention.

The present invention relates to pharmaceutical compositions comprising at least one acid addition salt of rotigotine and the use thereof, in particular for the use in a iontophoretic delivery system. It further relates to the use of these acid addition salts of rotigotine for the treatment of CNS disorders like Parkinson's Disease, and/or restless leg syndrome. It further relates to new rotigotine acid addition salts, in particular rotigotine dihydrogen phosphate.

BACKGROUND OF INVENTION

Rotigotine is the International Non-Proprietary Name (INN) of the compound (−)-5,6,7,8-tetrahydro-6-[propyl-[2-(2-thienyl)ethyl]-amino]-1-naphthalenol, having the structure shown below

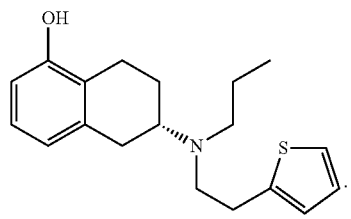 [SMILES: CCCN(CCc1cccs1)[C@H]1CCc2c(O)cccc2C1]

Rotigotine is a non-ergolinic D1/D2/D3 dopamine agonist that resembles dopamine structurally and has a similar receptor profile but a higher receptor affinity.

In contrast to other non-ergolinic dopamine agonists, rotigotine has significant D1 activity, which may contribute to a more physiological action.

In contrast to ergolinic compounds, rotigotine has a very low affinity for 5 $HT_2B$ receptors and thus a low risk of inducing fibrosis. Actions on non-dopaminergic receptors (such as 5-$HT_{1A}$ agonism and $A_{2B}$ antagonism) may contribute to other beneficial effects, such as antidyskinetic activity, neuroprotective activity and antidepressive effects.

Rotigotine is disclosed as active agent for treating patients suffering from Parkinson's disease (WO 2002/089777), Parkinson's plus syndrome (WO 2005/092331), depression (WO 2005/009424) and the restless-legs syndrome (WO 2003/092677) as well as for the treatment or prevention of dopaminergic neurone loss (WO 2005/063237).

Rotigotine has been tested in the form of its free base or as rotigotine hydrochloride.

The Restless Leg Syndrome (RLS) is a neurological disease that expresses itself as a false sensation in the legs accompanied by a strong kinetic urge. Symptoms of RLS include tingling, pulling, aching, itching, burning, cramps or pain, causing in the person concerned the irresistible urge to move. This disorder occurs most frequently when the person concerned is resting. Therapy studies have revealed a diversity of results obtained in monotherapeutic treatments with dopamine agonists, opiates, benzodiazepines, carbamazepine, clonidine or levodopa (L-DOPA) in combination with a dopa decarboxylase inhibitor. The use of L-DOPA for treating RLS has been the subject of a particularly large number of papers. Long-term L-DOPA therapy leads to a clear mitigation of the disorder with an improved quality of sleep and life. The drawback of most conventional monotherapies is that, depending on the duration of the therapy, the amount of the active ingredient must be progressively increased in order to ensure the success of the treatment. A surprising discovery has shown that the monotherapeutic administration of a rotigotine-containing transepicutaneous composition especially when in the form of a patch composition leads to the suppression and reduction of the RLS symptoms, with rotigotine as the active substance. Parkinson's disease is believed to be primarily caused by the degeneration of dopaminergic neurons in the substantia nigra. Parkinson's disease is primarily a disease of middle age and beyond, and it affects both men and women equally. The highest rate of occurrence of Parkinson's disease is in the age group over 70 years old, where Parkinson's disease exists in 1.5 to 2.5% of that population. The mean age at onset is between 58 and 62 years of age, and most patients develop Parkinson's disease between the ages of 50 and 79. There are approximately 800,000 people in the United States with Parkinson's disease. The clinical diagnosis of Parkinson's disease is based on the presence of characteristic physical signs. The disease is known to be gradual in onset, slowly progressive, and variable in clinical manifestation. Evidence suggests that the striatal dopamine content declines to 20% below levels found in age-matched controls before symptoms occur.

Treatment of Parkinson's disease has been attempted with, inter alia, L-dopa (levodopa), which still is the gold standard for the therapy of Parkinson's disease. Levodopa passes the blood-brain barrier as a precursor for dopamine and is then converted into dopamine in the brain. L-dopa improves the symptoms of Parkinson's disease but may cause severe side effects. Moreover, the drug tends to lose its effectiveness after the first two to three years of treatment. After five to six years, only 25% to 50% of patients maintain improvement. Furthermore a major drawback of currently utilized therapies for Parkinson's disease is the eventual manifestation of the "fluctuation syndrome", resulting in "all-or-none" conditions characterized by alternating "on" periods of mobility with dyskinesias and "off" periods with hypokinesia or akinesia.

Patients who display unpredictable or erratic "on-off" phenomena with oral anti-Parkinson therapy have a predictable beneficial response to i.v. administration of L-dopa and other dopamine agonists, suggesting that fluctuations in plasma concentrations of drug are responsible for the "on-off" phenomena. The frequency of "on-off" fluctuations has also been improved by continuous infusions of the dopamine receptor agonists apomorphine and lisuride. However, this mode of administration is inconvenient. Therefore, other modes of administration providing a more constant plasma level, such as topical administration, are beneficial and have been suggested in the past.

Transdermal drug delivery is an alternative for oral drug delivery and hypodermic injections. Different delivery methods have been investigated over the years to increase the drug delivery through the skin. Transdermal delivery is a well-established method of drug administration whereby the hepatic first-pass effect is circumvented. Several studies into the transdermal delivery of rotigotine have been carried out. The results showed a significant increase in bioavailability in comparison to oral delivery and providing a continuous delivery pattern. Monotherapy of rotigotine via passive diffusion controlled transdermal application is however limited by the skin permeability and may require dose titration to meet individual therapeutic needs. To date, various transdermal therapeutic systems (US) for the administration of rotigotine have been described.

WO 94/07468 discloses a transdermal therapeutic system containing rotigotine hydrochloride as active substance in a two-phase matrix which is essentially formed by a hydrophobic polymer material as a continuous phase and a disperse hydrophilic phase contained therein and mainly containing the drug and hydrated silica. The silica enhances the maximum possible loading of the US with the hydrophilic salt.

Moreover, the formulation of WO 94/07468 usually contains additional hydrophobic solvents, permeation-promoting substances, dispersing agents and, in particular, an emulsifier which is required to emulsify the aqueous solution of the active principle in the lipophilic polymer phase. A TTS, prepared by using such a system, has been tested in healthy subjects and Parkinson patients. The average drug plasma levels obtained by using this system were around 0.15 ng/mL with a 20 cm$^2$ patch containing 10 mg rotigotine hydrochloride. This level is considered too low to achieve a truly efficacious treatment or alleviation of the symptoms related to Parkinson's Disease.

Various further transdermal therapeutic systems (US) have been described for example in WO 99/49852. The US comprises a backing layer, inert with respect to the constituents of the matrix, a self-adhesive matrix layer containing an effective quantity of rotigotine or rotigotine hydrochloride and a protective film which is to be removed before use. The matrix system is composed of a non-aqueous polymer adhesive system, based on acrylate or silicone.

In the transdermal delivery system (TDS, which is used synonymous for US) according to WO94/07468 and many related applications, the drug crosses the membrane by passive diffusion. A disadvantage of these types of transdermal administration is that there is very limited dosing flexibility available, e.g. in view of individual dosing, limited maximum daily dose, on demand application, continuous or pulsatile administration pattern, period of administration.

However, as the skin is to be seen as a very efficient barrier for most drug candidates, such type of membrane controlled systems are more or less limited in practice to transdermal delivery of active substances that reveal a very high skin permeability. Additionally, special requirements on drug release kinetics have to be met like contact delivery over several days. The rotigotine flux obtained with these passive transdermal therapeutic systems is not necessarily sufficient for all patients.

Different delivery methods have been investigated over the years to increase the drug delivery through the skin.

There have been several attempts to increase the rates of transdermal drug delivery by using of alternative energy sources such as electrical energy and ultrasonic energy. Electrically assisted transdermal delivery is also referred to as electro transport. The term "electro transport" or "electromotive administration" as used herein refers generally to the delivery of an agent (e.g. a drug) through a membrane, such as skin, mucous membrane, or nails. One of the possibilities is iontophoresis. By applying a small current across the skin it is possible to enhance the transdermal delivery of small charged ionic molecules. Iontophoresis involves the application of an electromotive force to drive or repel ions through the dermal layers into a target tissue. Particularly suitable target tissues include those adjacent to the delivery site for localized treatment. Uncharged molecules can also be delivered using iontophoresis via a process called electroosmosis. This technology of "electro transport" offers several advantages over e.g. oral and injection or passive transdermal drug delivery. Key advantages of iontophoretic drug delivery include the avoidance of pain and potential for infection associated with needle injection, the ability to control the rate of drug delivery, the ability to programme the drug-delivery profile and the minimisation of local tissue trauma.

One of the interesting properties of this technique is the possibility to modulate the transport rate into and through the skin. This is an important advantage for drugs with a narrow therapeutic window, such as dopamine agonists.

Iontophoretic transdermal delivery relates to introducing ions or soluble salts of pharmaceutically active compounds into tissues of the body under the influence of an applied electric field.

In certain cases, e.g., when transdermal delivery by means of passive diffusion controlled patches appears to be ineffective or unacceptable because of low passage through the skin, leading to very large patches, iontophoretic transdermal delivery may provide an advantageous method of delivering that compound. Further iontophoretic transdermal delivery has the major advantage that the administered amount can be regulated precisely and can be used to easily titrate patients up to a certain level of administration over a period of up to several weeks.

Electrotransport devices use at least two electrodes that are in electric contact with some portion of the skin, nails, mucous membrane, or other surface of the body. One electrode, commonly called the "donor" electrode, is the electrode from which the agent is delivered into the body. The other electrode, typically termed the "counter" electrode, serves to close the electrical circuit through the body. For example, if the agent to be delivered is positively charged, i.e., a cation, then the anode is the donor electrode, while the cathode is the counter electrode which serves to complete the circuit. Alternatively, if an agent is negatively charged, i.e., an anion, the cathode is the donor electrode and the anode is the counter electrode. Additionally, both the anode and cathode may be considered donor electrodes if both anionic and cationic agent ions, or if uncharged dissolved agents, are to be delivered. Furthermore, electrotransport delivery systems generally require at least one (drug) reservoir or source of the agent to be delivered to the body.

Iontophoresis is well established for use in transdermal drug delivery. The advantage of this method is that unlike transdermal patches, it relies on active transportation within an electric field. It allows the delivery of water-soluble ionic drugs that are not effectively absorbed through the skin. In the presence of an electric field electromigration and electroosmosis are the dominant forces in mass transport. These movements are measured in units of chemical flux, commonly μmol/cm² h. There are a number of factors that influence iontophoretic transport including skin pH, drug concentration and characteristics, ionic competition, molecular size, current, voltage, time applied and skin resistance.

The advantage of this technique (e.g. iontophoresis) is that the flux can be accurately controlled and manipulated by the externally applied current. The level of enhancement that can be achieved is, for a large part, dependent on the charge, the lipophilicity, and the molecular weight of the drug. Compounds that enhance the percutaneous penetration of a drug have been applied widely in passive transdermal studies, although the applicability of these compounds in humans is limited by the level of skin irritation that they may evoke. Iontophoresis is a technique that allows movement of ions of soluble salts across a membrane under an externally applied potential difference that is induced across the skin by a low-voltage electric current. The application of current is controlled by an electronic device that adjusts the voltage in response to the changes in skin electrical resistance. Charged drug as well as other ions are carried across the skin as a component of induced ion flow. Numerous factors affect iontophoretic delivery, including flux proportionality with respect to applied current density and the presence of ions other than drug. Current up to 0.5 mA/cm² is believed to be tolerable for patients. The onset of action with iontophoretic treatment is rapid, in contrast to hours for passive transdermal delivery. Since drug delivery is proportional to applied current, significant advantages of iontophoresis include the possibility of preprogramming the drug delivery, dose tailoring on an individual basis, or time tailoring in a constant or pulsatile fashion.

Compared to passive transdermal delivery, iontophoresis provides for several advantages which are useful in the treatment of Parkinson's disease: it allows programming of the flux at the required therapeutic rate by adjusting the electric current. It is advantageous for a patient in need of a drug that the drug amount can be adjusted to the individual need. Another advantage is that iontophoresis allows for continuous as well as pulsatile administration and it permits a rapid start or termination of administration of the medication, if needed, by simply turning the iontophoretic delivery system on or off.

It is advantageous that control of the rate and duration of drug delivery can be handled in a way to avoid the potential risk of overdose and the discomfort of an insufficient dosage.

However, in any given electro transport process, more than one process, including at least some "passive" diffusion, may be occurring simultaneously to a certain extent. Accordingly, the term "electro transport" or "electromotive administration", as used herein, should be given its broadest possible interpretation so that it includes the electrically induced or enhanced transport of at least one agent, which may be charged, uncharged, or a mixture thereof, whatever the specific mechanism or mechanisms by which the agent actually is transported. For example the total iontophoretic flux consists of the passive flux ($J_{pass}$), the electro-osmotic flux ($J_{EO}$) and the electromigrative flux ($J_{EM}$). The latter two are representing the iontophotetic flux.

Another dopamine agonist which has been used in the treatment of Parkinson's disease is R-apomorphine. R-apomorphine is the International Non-Proprietary Name (INN) of the compound (R)-5,6,6a,7-tetrahydro-6-methyl-4H-dibenzoquinoline-11,12-diol. Several approaches to develop a system for iontophoretic administration of R-apomorphine have previously been described (see for example R. van der Geest, M. Danhof, H. E. Bodde "Iontophoretic Delivery of Apomorphine: In Vitro Optimization and Validation", Pharm. Res. (1997), 14, 1797-1802; M. Danhof, R. van der Geest, T. van Laar, H. E. Bodde, "An integrated pharmacokinetic-pharmacodynamic approach to optimization of R-apomorphine delivery in Parkinson's disease", Advanced Drug Delivery Reviews (1998), 33, 253-263). However, in spite of these efforts, only concentrations at the lower end of the therapeutic concentration range of 1.4 to 10.7 ng/ml could be obtained.

A further dopamine antagonist is ropinirole hydrochloride. Ropinirole (INN) is (4-[2-dipropylamina)ethyl]-1,3-dihydro-2H-indol-2-one). Although the iontophoretic administration of ropinirole was considered feasible, it was only possible to obtain fluxes at the lower end of the therapeutic range (see A. Luzardo-Alvarez, M. B. Delgado-Charro, J. Blanco-Mendez, "Iontophoretic Delivery of Ropinirole Hydrochloride: Effect of Current Density and Vehicle Formulation", Pharmaceutical Research (2001), 18 (12), 1714-1720).

WO2004/050083 relates to a method for treating or alleviating symptoms of Parkinson's disease, which uses iontophoretic delivery of the dopamine receptor agonist rotigotine. The composition used in the iontophoretic delivery system comprises rotigotine in form of its hydrochloride salt and at least one chloride salt in a concentration of 1 to 140 mmol/l the composition having a pH of 4 to 6.5. For an optimal performance a concentration of at least 0.5 mg/ml of the rotigotine hydrochloride is preferred, as derived from Example 1 and 2 of the European patent.

Although, investigating the transdermal iontophoretic delivery of rotigotine.HCl revealed that by applying an electrical current across the skin higher steady state fluxes can be achieved with a shorter lag time compared to passive delivery in these studies the maximum solubility of rotigotine.HCl in the donor phase appeared to be the limiting factor for its iontophoretic transport through the skin. It has been tried to increase the solubility of rotigotine by changing the donor solution, e.g. by adding surfactants or co-solvents or changing the source of Cl⁻ ions. A disadvantage of this iontophoretic delivery system is that e.g. an increase of sodium chloride concentration results in a decrease of the rotigotine flux.

A further limiting factor is the limited solubility of rotigotine hydrochloride in aqueous solvents as well as the strong salting out effect of e.g. sodium chloride.

Many patients need concentrations that are significantly higher than the ones feasible using iontophoretic delivery of the above mentioned compositions and/or are in need for an administration for a longer time period.

There is still a need to develop a transdermal delivery system providing on one hand a greater dosing flexibility (e.g. individual dosing) and on the other hand allowing continuous as well as pulsatile administration, if suitable for an extended period of time.

An object of the present invention is to control (i.e. to canalise/manoeuvre) the transport of rotigotine towards and across the skin from a drug reservoir, thereby optimizing the administration of the individual amount of rotigotine needed by the patient, enhancing the flux of rotigotine across the TDS/skin interface.

Another object and aspect of the present invention is to provide a suitable composition which lead to an enhanced delivery of rotigotine to and across the skin over a period of at least 24 hours, preferably longer than 24 hours.

Another object of the present invention is to provide a continuous as well as pulsatile delivery of the active compound across.

SUMMARY OF THE INVENTION

The present invention relates to iontophoretic transdermal technology that provides for the delivery of pharmaceutically acceptable rotigotine salts and compositions thereof through human skin.

The present invention provides pharmaceutical formulations suitable for iontophoresis that provide enhanced iontophoretic delivery of rotigotine to at least one target tissue. The formulations are further characterized by good to excellent solubility of the salts in aqueous solutions. The present invention also provides methods of administering rotigotine in at least one target tissue of and/or treating one of the diseases mentioned above in a patient by iontophoretically delivering a formulation of the invention.

The present invention provides a pharmaceutical formulation comprising at least one pharmaceutically acceptable acid addition salt of 6-(propyl-(2-thiophen-2-ylethyl)amino)tetralin-1-ol(rotigotine) and optionally a pharmaceutically acceptable electrolyte wherein said rotigotine salt has a saturation solubility in an aqueous solution which is at least 16 μmol/ml at a pH<6 and/or of at least 30 μmol/ml at a pH≤5.5, wherein all the above saturation solubilities are calculated based on the total amount of rotigotine in the pharmaceutically acceptable acid addition salt, with the proviso that the at least one pharmaceutically acceptable acid addition salt of rotigotine is not rotigotine.HCl.

The present invention further provides new pharmaceutically acceptable salts of rotigotine, like rotigotine dihydrogen phosphate, rotigotine dihydrogen citrate, rotigotine orotate, rotigotine 1-hydroxy-2-naphtoate, rotigotine hydrogen sulfate, rotigotine hydrogen tartrate, rotigotine sodium.

Surprisingly it has been found that due to an increase in the maximum solubility of pharmaceutically acceptable rotigotine salts, in particular rotigotine dihydrogen phosphate (rotigotine.$H_3PO_4$), an substantial increase in maximum flux, compared to rotigotine.HCl, can be achieved, that can be maintained for at least 24 hours, facilitating its application. In case of rotigotine dihydrogen phosphate the increase in the maximum solubility of rotigotine.$H_3PO_4$, a 170% increase in maximum flux, compared to rotigotine.HCl, was achieved, that can be maintained for at least 24 h, facilitating its application. A balance between solubility and delivery efficiency can be achieved by choosing the donor pH for example between 5 and 6. With ionthoporesis therapeutic levels can be achieved with a rapid onset time and maintained in a controlled manner by adjusting the current density.

It is further surprising that in one embodiment in contrast to the solubility of the rotigotine.HCl the presence of NaCl did not affect the solubility of the rotigotine salts of the present invention, e.g. rotigotine.$H_3PO_4$.

The present invention provides further two very important benefits of iontophoretic delivery of rotigotine in combination with iontophoresis over transdermal passive diffusion for symptomatic treatment of e.g. Parkinson's disease. Because of active transdermal delivery the onset time to achieve the desired level can be significantly decreased. Secondly by adjusting the current density a titration of the plasma concentration is possible, making it feasible to individually modulate the delivery according to the desired dosing regimen.

Using the parameters, determined by modeling the in vitro transport, in vivo simulations revealed that with iontophoresis therapeutic levels can be achieved with a rapid onset time and be maintained in a controlled manner by adjusting the current density.

Fluxes of around 50 μg/cm$^2$/hr can be achieved. A linear relationship between iontophoresis (steady state flux) and current density was obtained, which allows individual dose titration into the patient.

BRIEF DESCRIPTION OF THE DRAWINGS

FIG. 1 shows an exemplarily design of the iontophoresis cell.

FIG. 2 is a graph showing iontophoretic steady state flux±s.d. of rotigotine versus drug concentration.

FIG. 3 shows iontophoretic flux time profile of Rotigotine.$H_3PO_4$ dissolved in citric buffer pH 5.

FIG. 4 shows the correlation of the Flux$_{ss}$ during the passive phase (no current) and the iontophoretic phase (current density=500 μA·cm$^{-2}$) versus the donor concentration at different pHs.

FIG. 5 shows combined impact of donor solution pH and drug concentration on passive and iontophoresis transdermal steady state flux of rotigotine FIG. 6 shows impact of current density on transdermal steady state drug flux from donor solutions.

FIG. 7 is a graph showing population prediction of the simulations of iontophoretic delivery of rotigotine.$H_3PO_4$

DETAILED DESCRIPTION OF THE INVENTION

Figure 8:
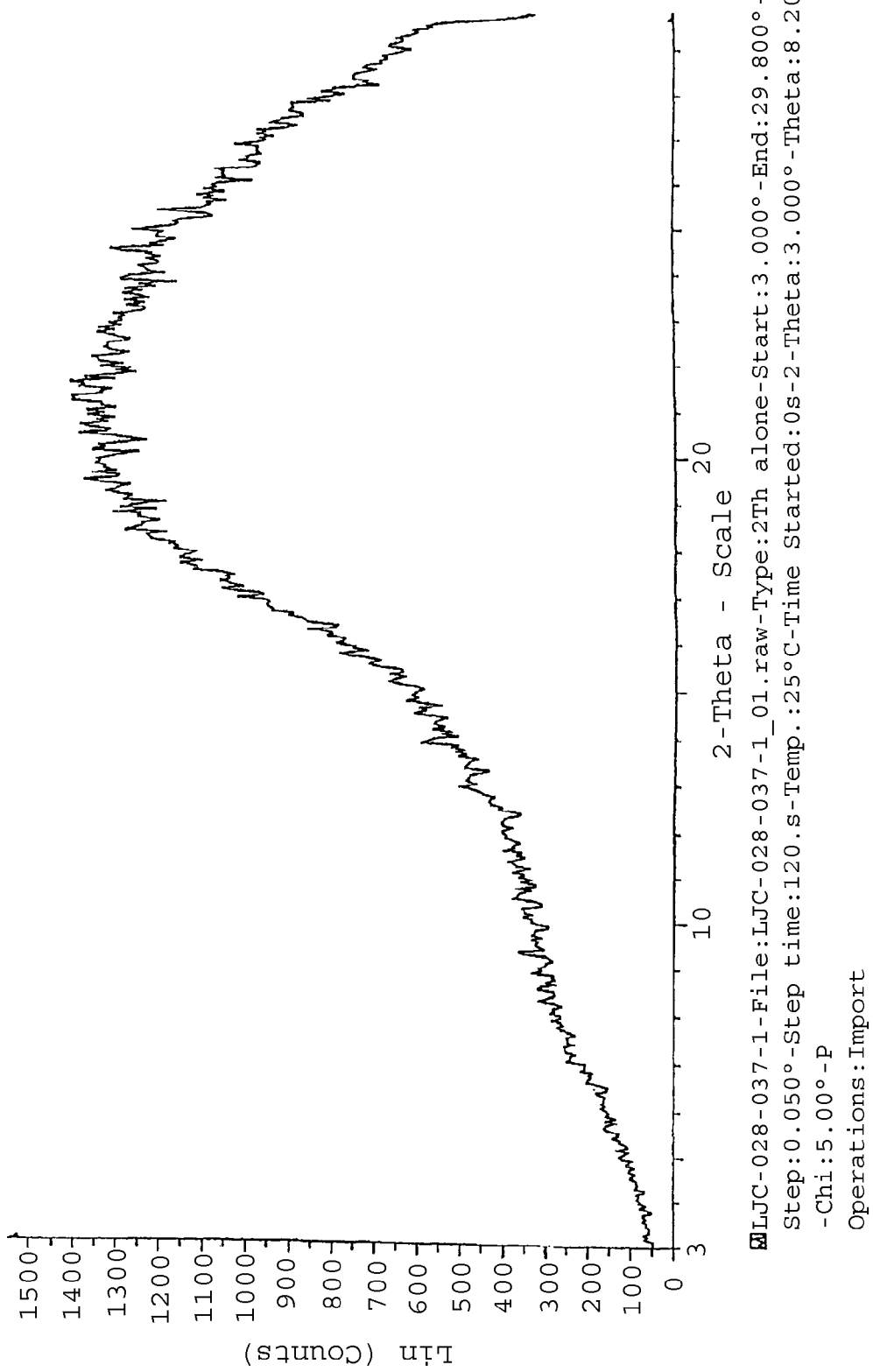
FIG. 8 shows a powder X ray diffractogram (XRPD) of rotigotine dihydrogen phosphate

The present invention relates to new salts of 6-(propyl-(2-thiophen-2-ylethyl)amino)tetralin-1-ol which is synonymous with the term rotigotine, In one aspect, the invention provides pharmaceutical formulations that are suitable for iontophoresis and that provide enhanced iontophoretic delivery of rotigotine to a patient, preferably a human patient, in need of treatment.

Thus, the invention relates to the iontophoretic delivery of rotigotine, including cathodal or anodal iontophoresis.

The present invention also relates to the use of compounds of the general formula I for the preparation of (a) a formulation for use in a device for transdermal administration by iontophoresis or kits containing cartridges which contain the compound ready for use in said device, (b) a device suitable for transdermal administration by iontophoresis, wherein said transdermal device has a reservoir containing the compound of formula I or a composition thereof and optionally a pharmaceutically acceptable electrolyte, which device can be used in a method for controlling the delivery profile of pharmaceutical compounds of the general formula I and compositions thereof, and the use of said controlled delivery profiles in the treatment of pain disorders, especially CNS disorders, especially Parkinson's disease, and restless leg syndrome.

Since rotigotine is a base, the salts of rotigotine are typically acid addition salts, e.g., citrate salts, phosphate salts, etc. The acid addition salts of rotigotine used in the formulations of the present invention typically have water solubilities of at least about 16 μmol/ml at a pH<6 and/or of at least about 30 μmol/ml at a pH≤5, wherein all the above saturation solubilities are calculated based on the total amount of rotigotine in the pharmaceutically acceptable acid addition salt. The acid addition salt of rotigotine dihydrogen phosphate typically has a water solubility of about 83 to 34 μmol/ml in a pH range of about 4 to 5.5. When the salts are placed in solution (e.g. aqueous solution), the salts dissolve and form protonated rotigotine cations and counter (e.g., citrate or phosphate) anions. As such, the rotigotine cations are delivered from the anodic electrode of an electrotransport delivery device.

In one embodiment, the concentration of the active agent, calculated as free base of rotigotine, in the formulation is at least about 16 μmol/ml of rotigotine at a pH<6, and/or such as at least about 30 μmol/ml of rotigotine at a pH≤5. In another embodiment the concentration of the active agent, calculated as free base of rotigotine, in the formulation is at least about 50 μmol/ml of rotigotine at a pH≤4

Where particular values are described in the application and claims, unless otherwise stated the term "about" means within an acceptable error range for the particular value as determined by one of ordinary skill in the art. In one embodiment, the term "about" means±10%, in another one ±5%, another one ±2%, another one ±1%, or another one ±0.5%.

One object of the present invention is to provide compounds of general formula I

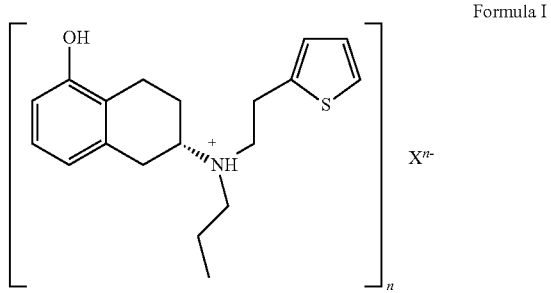

Formula I wherein $X^{n-}$ is the acid anion of a pharmaceutically acceptable inorganic or organic acid with the proviso that it is not rotigotine.HCl. The present invention relates to compounds of general formula I wherein $X^{n-}$ comprises mono and/or poly valent anions. There are certain acids having more than one acid protons which can be salified. For example citric acid has three carboxyl groups, all or part of which can be salified by the rotigotine base. Thus the formulation of the present invention can comprise monorotigotine dihydrogen citrate, dirotigotine hydrogen citrate or trirotigotine citrate or mixed citrates of rotigotine. The same applies to other acids addition salts like tartrates, sulfates, phosphates etc.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$. This does also apply to rotigotine in form of its free base For a skilled person the term (S)-6-(propyl(2-thiophen-2-yl)ethyl)amino)-5,6,7,8-tetrahydronaphthalen-l-ol tartrate (rotigotine tartrate) is synonymous with the term dirotigotine tartrate, (S)-6-(propyl(2-thiophen-2-yl)ethyl)amino)-5,6,7,8-tetrahydronaphthalen-1-ol citrate (rotigotine citrate) is synonymous with the term trirotigotine citrate and (S)-6-(propyl (2-thiophen-2-yl)ethyl)amino)-5,6,7,8-tetrahydronaphthalen-1-ol phosphate is synonymous with the term trirotigotine phosphate—if not stated otherwise.

Representative acid addition salts include, but are not limited to, acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrobromide, hydroiodide, 2-hydroxyethansulfonate (isothionate), 1-hydroxy-naphtoate, lactate, maleate, mesylate, methane sulfonate, nicotinate, 2-naphthalene sulfonate, orotate, oxalate, palmitoate, pectinate, persulfate, 3-phenylpropionate, picrate, pivalate, propionate, phosphate, succinate, tartrate, thiocyanate, phosphate, glutamate, bicarbonate, p-toluenesulfonate and sulphate, all of the foregoing comprising all variations from partly salified to completely salified.

In one embodiment the acid addition salt is not (S)-6-(propyl(2-thiophen-2-yl)ethyl)amino)-5,6,7,8-tetrahydronaphthalen-1-ol hydrobromide, (S)-6-(propyl(2-thiophen-2-yl)ethyl)amino)-5,6,7,8-tetrahydronaphthalen-1-ol p-toluensulfonate, (S)-6-(propyl(2-thiophen-2-yl)ethyl)amino)-5,6,7,8-tetrahydronaphthalen-l-ol heminaphthalene-1,5-disulfonate, (S)-6-(propyl(2-thiophen-2-yl)ethyl)amino)-5,6,7,8-tetrahydronaphthalen-1-ol tartrate, and (S)-6-(propyl(2-thiophen-2-yl)ethyl)amino)-5,6,7,8-tetrahydronaphthalen-1-ol phosphate.

In another embodiment the acid addition salt is further not (S)-6-(propyl(2-thiophen-2-yl)ethyl)amino)-5,6,7,8-tetrahydronaphthalen-1-ol citrate, (S)-6-(propyl(2-thiophen-2-yl) ethyl)amino)-5,6,7,8-tetrahydronaphthalen-1-ol sulfate and (S)-6-(propyl(2-thiophen-2-yl)ethyl)amino)-5,6,7,8-tetrahydronaphthalen-1-ol methanesulfonate.

More specifically the invention is related to pharmaceutical compounds of the general formula I selected from dirotigotine hydrogen phosphate, rotigotine dihydrogen phosphate, rotigotine dihydrogen citrate, dirotigotine hydrogen citrate, rotigotine orotate, rotigotine 1-hydroxy-2-naphtoate, rotigotine hydrogen sulfate, rotigotine sulphate, rotigotine hydrogen tartrate or mixtures thereof.

In another embodiment the acid addition salt is selected from rotigotine dihydrogen phosphate, rotigotine dihydrogen citrate, rotigotine orotate, rotigotine 1-hydroxy-2-naphtoate, rotigotine hydrogen sulphate, rotigotine hydrogen tartrate or mixtures thereof.

Even more specifically the invention is related to the use of at least one compound of the general formula I as defined above, or mixtures thereof, for the manufacture of an medicament for the treatment of fibromyalgia, restless leg syndrome and CNS disorders, especially Parkinson's disease.

The present invention relates to transdermal iontophoretic delivery of pharmaceutical compounds of general formula I wherein $X^{n-}$ comprises mono and/or poly valent anions. More specifically the invention is related to transdermal iontophoretic delivery of pharmaceutical compounds of the general formula I wherein the salt is dirotigotine hydrogen phosphate, rotigotine dihydrogen phosphate, rotigotine dihydrogen citrate, dirotigotine hydrogen citrate, rotigotine orotate, rotigotine 1-hydroxy-2-naphtoate, rotigotine hydrogen sulfate, rotigotine sulphate, rotigotine hydrogen tartrate, rotigotine tartrate or mixtures thereof.

In one embodiment of transdermal iontophoretic delivery of pharmaceutical compounds of general formula I, $X^{n-}$ is selected from the acid anion of methane sulphonic acid, benzene sulphonic acid, phosphoric acid, tartaric acid, gluconic acid, citric acid, malic acid, lactic acid, benzoic acid, adipic acid, maleic acid, aspartic acid, fumaric acid, succinic acid, sulphuric acid, orotic acid, 1-hydroxy-naphtoic acid. In another embodiment $X^-$ is selected from the acid anion of phosphoric acid, sulphuric acid, orotic acid, 1-hydroxy-naphtoic acid, citric acid, tartaric acid, in particular dihydrogen phosphate.

As stated above, the compounds of formula I can be used in the form of pharmaceutically acceptable salts derived from inorganic or organic acids. Salts of prodrugs also fall within the scope of this invention. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

These compounds are suitable for use as a medicament in particular for treating CNS disorders like Parkinson Disease, fibromyalgia, restless leg syndrome, depression and/or Parkinson's accessory symptoms. They are suitable for use in a transdermal delivery system. Such transdermal delivery system can for example be a patch, an electro transport device, inotophoretic delivery system.

One object of the present invention is to provide stable salts of rotigotine with improved solubilities in solutions at a pH of less than 6. Rotigotine as the free base has high solubility in common organic solvents, but low solubility in water.

Under the conditions according to the present invention it is possible to maintain a pharmaceutical composition with a higher concentration of an effective amount of rotigotine without the need of further adding salt(s)(ions), e.g. chloride salts. A disadvantage of the systems known in the art is a salting out effect which decreases the available rotigotine transport through the skin. In previous attempts one of the major limitations in the iontophoretic transport of rotigotine-.HCl was its low solubility. For example the maximum solubility of rotigotine.HCl was only 22.4 µmol/ml (in absence of further chloride salts) at pH 5 and in the presence of 0.07 molar NaCl the maximum solubility of rotigotine.HCl decreased to 6.3 µmol/ml at pH 5. In that study the iontophoretic transport at varying rotigotine.HCl concentrations between 1.4 and 3.9 µmol/ml showed a linear relationship between the $Flux_{ss}$ and the donor concentration. This demonstrated that the maximum iontophoretic flux of rotigotine was not yet achieved, but the low solubility of rotigotine.HCl prevented further increase in the iontophoretic flux.

The solubility of rotigotine is an important determinant of the maximum drug concentration. The problem of a rotigotine acid addition salt having a maximum solubility in an aqueous solution at a pH of about 6 of less than 16 µmol/ml or having a maximum solubility in an aqueous solution at a pH of about 5.5 of less than 30 µmol/ml (calculated based on the total amount of rotigotine in the pharmaceutically acceptable acid addition salt) like rotigotine.HCl is that their use for electro transport is limited due to a low or poor iontophoretic transportation rate. Another disadvantage is the negative impact of the addition of chloride salts on solubility of rotigotine.HCl and therefore on the available rotigotine concentration available for skin permeation.

Surprisingly, it was found that certain acid addition salts of rotigotine are more soluble than the rotigotine hydrochloride salt form and are thus particularly suited for pharmaceutical compositions for use in transdermal electrotransport, e.g. iontophoresis. Suitable rotigotine salts for transdermal electrotransport are for example the ones mentioned herein. In one embodiment the salts are selected from the orotate, citrate (including hydrogen citrate, dihydrogen citrate) tartrate (including hydrogen tartrate, tartrate), phosphates (including dihydrogen phosphate, hydrogen phosphate and phosphate) of rotigotine. In one embodiment the salt is selected from the hydrogen sulfate, orotate, dihydrogen citrate, hydrogen tartrate, in particular hydrogen L-tartrate and/or dihydrogen phosphate of rotigotine. In another embodiment the salt is selected from the orotate, hydrogen tartrate, in particular hydrogen L-tartrate and/or dihydrogen phosphate of rotigotine. In still another embodiment the pharmaceutically acceptable salt is rotigotine dihydrogen phosphate which has the formula:

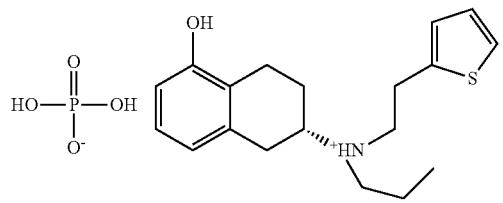 [SMILES: O=P([O-])(O)O ; CCC[NH+](CCc1cccs1)[C@H]1CCc2c(O)cccc2C1]

One embodiment comprises a pharmaceutical formulation comprising at least one pharmaceutically acceptable acid addition salt of 6-(propyl-(2-thiophen-2-ylethyl)amino)tetralin-1-ol(rotigotine) and optionally a pharmaceutically acceptable electrolyte wherein said rotigotine salt has a saturation solubility in an aqueous solution which is at least about 16 µmol/ml at a pH<6 wherein all the above saturation solubilities are calculated based on the total amount of rotigotine in the pharmaceutically acceptable acid addition salt, with the proviso that the at least one pharmaceutically acceptable acid addition salt of rotigotine is not rotigotine.HCl, in particular a pharmaceutical composition comprising at least rotigotine dihydrogen phosphate as a rotigotine acid addition salt. In another embodiment the pharmaceutical composition comprises at least one pharmaceutically acceptable acid addition salt of rotigotine characterized in that the at least one pharmaceutically acceptable acid addition salt of rotigotine has a saturation solubility in an aqueous solution which is at least about 30 µmol/ml at a pH≤5.5, in particular a pharmaceutical composition comprising at least rotigotine dihydrogen phosphate. In another embodiment the pharmaceutical composition comprises at least one pharmaceutically acceptable acid addition salt of rotigotine characterized in that the at least one pharmaceutically acceptable acid addition salt of rotigotine has a saturation solubility in an aqueous solution which is at least about 40 µmol/ml at a pH≤5, in particular a pharmaceutical composition comprising at least rotigotine dihydrogen phosphate. All the above saturation solubilities are calculated based on the total amount of rotigotine in the pharmaceutically acceptable acid addition salt.

Other salts which can be used in the pharmaceutical compositions according to the present invention are disclosed further above and in the claims. In one embodiment, the pharmaceutical composition comprises said rotigotine acid addition salt, which is not the HCl, the tartrate or the phosphate salt of rotigotine. In just another embodiment, the pharmaceutical composition comprises said rotigotine acid addition salt which is not the rotigotine HCl salt, for use in a transdermal electrotransport system. Another aspect is the use of said acid addition salts of rotigotine in the preparation of an iontophoretic device. Another aspect of the present invention is an iontophoretic device comprising a pharmaceutical composition as described further above. Another aspect of the invention is the use of said pharmaceutical compositions as described herein for the manufacturing of a transdermal medicament or device, particularly an iontophoretic device.

The temperature range wherein the saturation solubility is provided is usually in the range of about 15-40° C. In one embodiment it is in the range of about 18-38° C. and in another one in the range of about 18-25° C.

In an embodiment, desirable solutions for iontophoresis have all drug in solution and the concentration of the drug should not be too near the drug solubility limit. If the drug concentration is near the solubility limit small changes in temperature or composition can result in drug precipitation.

In order to avoid precipitation of the at least one pharmaceutically acceptable salt of rotigotine in one embodiment the amount of the rotigotine salt present is less than the amount necessary to achieve saturation of the solution. In another embodiment a pharmaceutical composition according to invention comprises the at least one pharmaceutically acceptable salt of rotigotine in an amount of at least 80% of the amount necessary to achieve saturation. In another embodiment the amount is at least 90% of the amount necessary to achieve saturation.

In one embodiment the pH of the pharmaceutical composition is less than 6, in another one pH≤5.5 and yet another one pH≤5. In another embodiment the pH is in the range of 3 to 5.9 and in another one in the range of 4 to 5.5. In one embodiment the saturation solubility of the rotigotine salt is at least 30 μmol/ml within the range of 4 to 5.5.

The pH of the solution in the drug reservoir may be at least about 3.0 in some embodiments. In other embodiments, the pH may be less than or equal to about 6. In still other embodiments, the pH may range from about 4.0 to about 5, 9 or 6. The pH can be maintained on a constant level by means of a buffer such as a citrate buffer or a phosphate buffer.

In one embodiment the pharmaceutical composition further comprises a buffer solvent. Suitable buffer solvents are all buffers which provide that the pH of the solution changes very little when a small amount of acid or base is added within the requested pH range. This includes pH ranges of ≤6. Suitable buffers are for example HCl, Sodium citrate, Citric acid/Sodium citrate, Acetic acid/Sodium acetate, Citric acid/$Na_2HPO_4$.

In one embodiment, the pharmaceutically acceptable rotigotine salt is formulated in a buffer at a pH between about 3 and 6 (preferably between about 4 and 5.9) or between 5 and 6 (preferably between about 5 and 5.9).

The term "buffer" refers to solutions of compounds that are known to be safe for pharmaceutical or veterinary use in formulations and that have the effect of maintaining or controlling the pH of the formulation in the pH range desired for the formulation.

In the drug reservoir, the concentration of the pharmaceutically acceptable salt of rotigotine may be, for example, is at least about 16 μmol/ml at a pH<6, wherein the concentration is calculated based on the total amount of rotigotine in the pharmaceutically acceptable acid addition salt, with the proviso that the at least one pharmaceutically acceptable acid addition salt of rotigotine is not rotigotine.HCl. The concentration of the rotigotine salt in the drug reservoir may be, for example in another embodiment, at least about 30 μmol/ml at a pH≤5.5 and in still another embodiment the concentration of the rotigotine salt in the drug reservoir may be about 40 μmol/ml at a pH≤0.5.

Additionally, the drug reservoir of the iontophoretic system may include further additives. Such additives can be chosen from those that are well known and conventional in the iontophoresis art. Such additives include, for example, antimicrobial agents, preservatives, antioxidants, penetration enhancers and buffers.

It has surprisingly been found that the iontophoretic delivery (dose and profile) by which a particular active compound of the general formula (I) is administered to a patient may be controlled by suitable combination of the initial concentration of the drug and electrolyte and the applied current (constant/variable) in the iontophoretic system. For example, it has been found that the combination of current density (constant/variable) and the initial amount of electrolyte may lead to an iontophoretic device with a very reasonable size that allows the drug delivery profile to be adjusted.

The ability to tailor the drug delivery profile in iontophoresis may provide increased control of the drug's effects on the user. Additionally, the ability to tailor drug delivery profile in iontophoresis may make the iontophoretic delivery of the compounds of formula (I) a more practically effective mode of administration.

For the purposes of electromotive administration, and in particular of iontophoretic administration, the pharmaceutically acceptable rotigotine salt, in addition to its aqueous solution form, can also be formulated in any form in which the rotigotine ions are free to move. In such formulations the medicament can be incorporated into a gel (such as gelatin), a hydrogel, a gum, a foam, or a nonionic cream so as to make the iontophoresis process convenient.

Silver anodic electrodes have been proposed for transdermal electrotransport delivery as a way to maintain pH stability in the anodic reservoir. One of the shortcomings of using a silver anodic electrode in an electrotransport delivery device, namely that the application of current through the silver anode causes the silver to become oxidized ($Ag\rightarrow Ag^+ + e^-$) thereby forming silver cations which compete with the cationic drug for delivery into the skin by electrotransport. Silver ion migration into the skin results in a transient epidermal discoloration (TED) of the skin. Therefore in some embodiments supplementary chloride ion sources like chloride salts are included in the formulation of the present invention. These chlorides are effective at providing sufficient chloride for preventing silver ion migration, and the attendant skin discoloration when delivering rotigotine transdermally by electrotransport using a silver anodic electrode.

To feed the electrochemical reaction at the anodal side using a Ag/AgCl electrode chloride salts as electrolytes are often added to the donor solution. Examples of suitable electrolytes include all $Cl^-$ donating compounds that are water soluble, such as HCl, NaCl, KCl, $CaCl_2$, $MgCl_2$, triethylammonium chloride and tributylammonium chloride. In one embodiment the suitable electrolytes include all $Cl^-$ donating compounds that are water soluble with the proviso that it is not rotigotine.HCl. In one embodiment the electrolyte comprises NaCl. The required amount of electrolyte may depend on factors such as the transport area of the device, the volume of the vehicle or carrier, the concentration of the active compound, the current density, the duration of the iontophoresis and the efficiency of the transport. A suitable chloride concentration is within the range of 1 to 140 mmol/l, preferably 50 to 100 mmol/l, more preferably 60 to 80 mmol/l. In other embodiments the electrolyte may be present in amounts of, for example, at least about 0.005 mmole, at least about 0.01 mmole, or at least about 0.05 mmole. The electrolyte may be present in amounts of, for example, not more than about 2 mmole, not more than about 1.0 mmole, or not more than about 0.3 mmole. The initial amount of electrolyte may be expressed as a concentration of, for example, at least about 0.005 M, at least about 0.01 M, or at least about 0.03 M. The initial amount of electrolyte may be expressed as a concentration of, for example, not more than about 2 M, not more than about 0.2 M, or not more than about 0.02 M.

The composition as described herein can be used in the donor phase of an iontophoretic device. Usually the donor phase is contained in a donor reservoir. Any conventional iontophoretic device may be used in the invention. Such iontophoretic devices are described e.g. in V. Nair, O. Pillai, R. Poduri, R. Panchagnula, "Transdermal Iontophoresis. Part I: Basic Principles and Considerations" Methods Find. Exp. Clin. Pharmacol. (1999), 21 (2), 139-151.

The drug reservoir contains the drug and optional electrolyte with, as the vehicle or carrier, either an aqueous solution or a (hydro) gel. The reservoir gel may be comprised of water soluble polymers or hydrogels. In principle any gel can be used.

The composition according to the present invention is mostly used in the donor phase of the iontophoretic device.

In some embodiments, the iontophoretic system comprises (a) a transdermal delivery device attachable to the skin, the device comprising a first electrode and a second electrode, and a reservoir capable of comprising a compound of the formula I as set forth above, and optionally a pharmaceutically acceptable electrolyte, in electrical communication with the first and second electrodes, and (b) means for connecting an electrical power source to the first and second electrodes.

The iontophoretic device offers the possibility to enhance the transdermal transport of in particular polar electrically charged drugs. In addition to increasing drug transport, iontophoresis offers the possibility to deliver the drug in a programmed way. This is important in the treatment of Parkinson's disease in which, due to a narrow therapeutic window, accurate individualized dosing is crucial. Therefore, it is possible that the iontophoretic device provides a pulsatile or continuous administration.

In one embodiment a pharmaceutical composition according to the present invention used for transdermal administration, in particular when used for iontophoretic administration, can be used for pulsatile as well as for continuous administration.

In one embodiment of present invention of a pharmaceutical composition is suitable for the treatment of Parkinson's disease, Restless Syndrome, Depression, Fibromyalgia and/or Parkinson's accessory symptoms. In another embodiment the pharmaceutical composition is used in an iontophoretic device for administration via electro transport for the treatment of Parkinson Disease and/or RLS.

The formulations are preferably administered via iontophoresis. The current density employed during iontophoresis may be varied according to the patient's needs and will depend on the iontophoretic device and the composition used. A suitable current may be determined by the attendant physician. For example the current density can be at a level from about 0.001 to about 1.0 mA/cm$^2$. In general, a suitable current density will be in the range of preferably 200 to 500 μA/cm$^2$. In one embodiment the current density is in the range of 250 to 400 μA/cm$^2$. In another embodiment the current density is in the range of 300 to 380 μA/cm$^2$.

In one embodiment, a current density of at least 150 μA/cm$^2$ is applied, in another one at least 167 μA/cm$^2$, in another one at least 300 μA/cm$^2$, in another one at least 350 μA/cm$^2$, in another one at least 500 μA/cm$^2$.

In one embodiment, a flux of at least about 12 μg/cm$^2$/h, in another one a flux of at least about 20 μg/cm$^2$/h, a flux of at least about 30 μg/cm$^2$/h, a flux of at least about 40 μg/cm$^2$/h is achieved. The iontophoresis can be applied for a sufficient time to achieve an effective amount of drug in the skin.

During the delivery period, the current may be caused to flow by applying a constant or variable, such as pulsed or alternating voltage/current. Alternatively, the current may be caused to increase during the delivery period in order to titrate an increasing concentration of the compound of formula (I).

The voltage charged in the current application step is selected in the range of voltage that does not injure the skin of a living body and that does not disadvantage the rate of the transdermal absorption of the active compound. The voltage can be, for example, at least about 0.1 V, or at least about 0.5 V, or at least about 1 V. The voltage also can be, for example, less than about 40 V, or less than about 20 V, or less than about 10 V.

The pulsed or alternating voltage may have a frequency of, for example, at least about 0.01 Hz, or at least about 100 Hz, or at least about 5 kHz. The pulsed or alternating voltage may have a frequency of, for example, no more than about 200 kHz, or no more than about 100 kHz, or no more than about 80 kHz. The pulsed or alternating voltage may use substantially any type of waveform shape, including for example, sine, square, triangular, sawtooth, rectangular, etc. In addition, the pulsed or alternating voltage may be applied on a duty cycle less than 100%.

The maximum amount of rotigotine salt that can dissolve at room temperature in a specific volume represents the saturation solubility or maximum solubility which are used synonymous.

The present invention further relates to the following embodiments which are not exhaustive:

1. A pharmaceutical formulation comprising at least one pharmaceutically acceptable acid addition salt of 6-(propyl-(2-thiophen-2-ylethyl)amino)tetralin-1-ol(rotigotine) and optionally a pharmaceutically acceptable electrolyte wherein said rotigotine salt has a saturation solubility in an aqueous solution which is at least 16 μmol/ml at a pH<6 and/or of at least 30 μmol/ml at a pH 5, wherein all the above saturation solubilities are calculated based on the total amount of rotigotine in the pharmaceutically acceptable acid addition salt with the proviso that said salt is not rotigotine.HCl.
2. A pharmaceutical formulation according to embodiment 1 wherein the electrolyte is a chloride salt.
3. A pharmaceutical formulation according to embodiment 2 with the proviso that the electrolyte is not rotigotine.HCl.
4. A pharmaceutical formulation according to any of the preceding embodiments wherein the electrolyte is selected from NaCl, KCl, CaCl$_2$, MgCl$_2$, triethylammonium chloride and/or tributylammonium chloride.
5. A pharmaceutical formulation according to any of the preceding embodiments wherein the concentration of the chloride salt is at least about 1 mmol/l.

6. A pharmaceutical formulation according to any of the preceding embodiments wherein the concentration of the chloride salt is about 1 to 140 mmol/l.
7. A pharmaceutical formulation according to according to any of the preceding embodiments wherein the pH of the pharmaceutical formulation is <6.
8. A pharmaceutical formulation according to according to any of the preceding embodiments wherein the pH of the pharmaceutical formulation is ≤5.
9. A pharmaceutical formulation according to any of the preceding embodiments comprising a solution with a pH in a range of about 4-6.
10. A pharmaceutical formulation according to any of the preceding embodiments wherein the saturation solubility in an aqueous solution is provided at about 15-40° C.
11. A pharmaceutical formulation according to any of the preceding embodiments wherein the saturation solubility in an aqueous solution is provided at about 18-38° C.
12. A pharmaceutical formulation according to any of the preceding embodiments wherein the saturation solubility in an aqueous solution is provided at about 18-25° C.
13. A pharmaceutical formulation according to any of the preceding embodiments wherein the pharmaceutical formulation comprises the at least one pharmaceutically acceptable salt of rotigotine in an amount of less than 100% of the amount necessary to achieve saturation.
14. A pharmaceutical formulation according to any of the preceding embodiments wherein the pharmaceutical formulation comprises the at least one pharmaceutically acceptable salt of rotigotine in an amount of at least 80% of the amount necessary to achieve saturation.
15. A pharmaceutical formulation according to any of the preceding embodiments wherein the pharmaceutical formulation comprises the at least one pharmaceutically acceptable salt of rotigotine in an amount of at least 90% of the amount necessary to achieve saturation.
16. A pharmaceutical formulation according to any of the preceding embodiments further comprising a buffer solvent.
17. A pharmaceutical formulation according to embodiment 16 wherein the buffer is a citrate buffer.
18. A pharmaceutical formulation according to any of the preceding embodiments wherein the at least one pharmaceutically acceptable acid addition salt of rotigotine is selected from dirotigotine hydrogen phosphate, rotigotine dihydrogen phosphate, rotigotine dihydrogen citrate, dirotigotine hydrogen citrate, rotigotine orotate, rotigotine 1-hydroxy-2-naphtoate, rotigotine hydrogen sulfate, rotigotine sulphate, rotigotine hydrogen tartrate.
19. A pharmaceutical formulation according to any of the preceding embodiments wherein the at least one pharmaceutically acceptable acid addition salt of rotigotine is rotigotine dihydrogen phosphate.
20. Use of a pharmaceutical formulation according to any of the preceding embodiments for application in a transdermal delivery system.
21. Use of a pharmaceutical formulation according to any of the preceding embodiments for application in an electro transport device for transdermal administration.
22. Use of a pharmaceutical formulation according to any of the preceding embodiments for application in a transdermal delivery system wherein the system is an iontophoretic system.
23. Use of a pharmaceutical formulation according to any of the preceding embodiments, wherein the formulation is used in a donor phase.
24. Use of a pharmaceutical formulation according to embodiment 21 to 23 wherein the said device is able to deliver a constant and/or variable current during the current application step in the transdermal administration.
25. Use of a pharmaceutical formulation according to embodiment 21 to 24 wherein the iontophoretic device provides a pulsatile or continuous administration.
26. Use of a pharmaceutical formulation according to embodiment 20 to 25 wherein the flux is at least 43 μg/cm²/h at a concentration of at least 13 μmol/ml of the at least one pharmaceutically acceptable acid addition salt rotigotine at a pH 6 and/or the flux is at least 47.9 μg/cm²/h at a concentration of at least 31 μmol/ml of the at least one pharmaceutically acceptable acid addition salt rotigotine at a pH 5.5 and/or the flux is at least 37 μg/cm²/h at a concentration of at least 22 μmol/ml of the at least one pharmaceutically acceptable acid addition salt rotigotine at a pH 5 wherein all the above concentrations are calculated based on the total amount of rotigotine in the pharmaceutically acceptable acid addition salt.
27. Use of the of a pharmaceutical formulation according to any of the preceding embodiments for the prevention or treatment of CNS disorders like Parkinson's disease, Restless Legs Syndrome, Parkinson Plus Syndrome, depression, fibromyalgia and/or Parkinson's accessory symptoms.
28. Compounds of general formula I

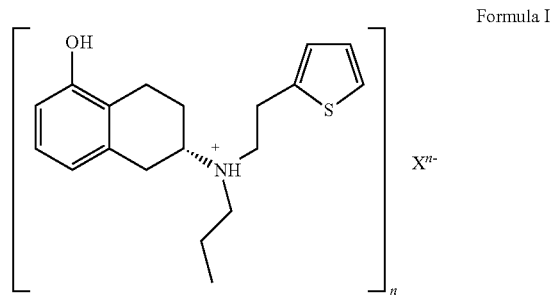

Formula I wherein $X^{n-}$ is the acid anion of a pharmaceutically acceptable inorganic or organic acid and wherein n is 1-5 with the proviso that it is not rotigotine.HCl.
29. Compound according to embodiment 28 with the further proviso that formula I is not (S)-6-(propyl(2-thiophen-2-yl)ethyl)amino)-5,6,7,8-tetrahydronaphthalen-1-ol hydrobromide, (S)-6-(propyl(2-thiophen-2-yl)ethyl)amino)-5,6,7,8-tetrahydronaphthalen-1-ol p-toluensulfonate, (S)-6-(propyl(2-thiophen-2-yl)ethypamino)-5,6,7,8-tetrahydronaphthalen-1-ol heminaphthalene-1,5-disulfonate, (S)-6-(propyl(2-thiophen-2-yl)ethyl)amino)-5,6,7,8-tetrahydronaphthalen-l-ol tartrate, (S)-6-(propyl(2-thiophen-2-yl)ethyl)amino)-5,6,7,8-tetrahydronaphthalen-l-ol citrate, rotigoine methane sulphonic acid and (S)-6-(propyl(2-thiophen-2-yl)ethyl)amino)-5,6,7,8-tetrahydronaphthalen-l-ol phosphate.
30. Compounds according to embodiment 28 or 29, characterized in that $X^{n-}$ is selected from the acid anion of, benzene sulphonic acid, phosphoric acid, gluconic acid, citric acid, malic acid, lactic acid, benzoic acid, adipic acid, maleic acid, aspartic acid, fumaric acid, succinic acid, sulphuric acid, orotic acid, 1-hydroxy-naphtoic acid.
31. Compounds according to embodiment 28 to 30 wherein the $X^{n-}$ is selected from the acid anion of phosphoric acid, sulphuric acid, orotic acid, 1-hydroxy-naphtoic acid, citric acid and/or tartaric acid.

32. Compounds according to embodiment 28 to 31 wherein the compound of formula I is rotigotine dihydrogen phosphate.

33. A compound of general formula II

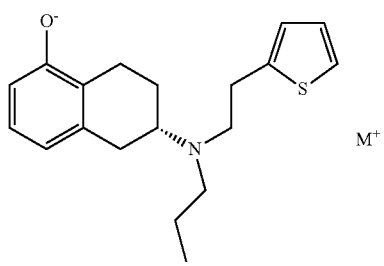

Formula II wherein M⁺ is selected from Na⁺, K⁺ and/or arginate.

34. A compound according to embodiment 33 wherein M⁺ is Na⁺.

35. Compound according to embodiment 28 to 34 for use as a medicament.

36. Compound according to any of embodiment 28 to 34 for manufacturing a pharmaceutical product for the treatment of CNS disorders, Parkinson Disease, fibromyalgia, restless leg syndrome, depression and/or Parkinson's accessory symptoms.

37. Pharmaceutical formulation comprising a compound according to embodiment 28 to 34.

38. Use of a compound according to any of embodiment 28 to 34 for the use in a transdermal delivery system.

39. Use according to embodiment 38 wherein the transdermal delivery system is a patch.

40. Use according to embodiment 38 wherein the transdermal delivery system is an iontophoretic device.

41. Use according to embodiment 38, wherein the embodiment does not apply to rotigotine tartrate or rotigotine phosphate.

42. The use of at least one compound of the general formula I or formula II according to any of embodiments 28 to 34 or a mixture thereof, and optionally a pharmaceutically acceptable electrolyte, for the manufacture of an iontophoretic device for the prevention or treatment of CNS disorders, Parkinson Disease, fibromyalgia, restless leg syndrome, depression and/or Parkinson's accessory symptoms.

43. The use according to embodiment 42, wherein said iontophoretic device has a reservoir containing the compound of formula I or a composition thereof or formula II or a composition thereof and optionally a pharmaceutically acceptable electrolyte.

44. The use according to any of embodiments 42-43, wherein the compound of formula I and the optional electrolyte are dissolved in a vehicle or carrier consisting of an aqueous solution or a gel.

45. The use according to embodiment 43 or 44, wherein the iontophoretic device additionally contains a membrane which separates the vehicle or carrier from the skin when applied for transdermal administration by iontophoresis.

46. The use according to embodiments 42-45, characterized in that said iontophoretic device is able to deliver a constant current during the current application step in the transdermal administration by iontophoresis.

47. The use according to embodiments 42-46, characterized in that said iontophoretic device is able to deliver a variable current during the current application step in the transdermal administration by iontophoresis.

48. The use according to embodiment 46 or 47, characterized in that said iontophoretic device is able to deliver an increasing current during the current application step in the transdermal administration by iontophoresis.

49. The use according to embodiments 42-48, characterized in that said iontophoretic device is able to deliver a current density at a level from about 0.001 to about 1.0 mA/cm².

50. The use according to embodiments 49, characterized in that said iontophoretic device is able to deliver a current density at a level from about 200 to 500 µA/cm².

51. The use according to embodiments 42-50, characterized in that said iontophoretic device is able to deliver fluxes of around 50 µg/cm²/hr.

52. The use according to embodiments 42-51, wherein the compound concentration in the solution is 4.4 mM to 47.5 mM, buffered at pH 5 and/or
    wherein the compound concentration in the solution corresponds to concentrations rotigotine free base of 1.4 mg/ml to 15 mg/ml, buffered at pH 5 and/or
    wherein compound concentration in the solution is 4.4 mM to 13.5 mM, buffered at at pH 6 and/or
    wherein the compound concentration in the solution corresponds to concentrations rotigotine free base of 1.4 mg/ml to 4.3 mg/ml, buffered at pH 6.

53. The use according to embodiments 42-52, wherein the compound of formula I is rotigotine dihydrophosphate.

54. The use according to embodiments 42-52, wherein the compound of formula I is rotigotine orotate.

55. The use according to embodiments 42-52, wherein the compound of formula I is rotigotine hydrogen sulphate.

56. The use according to embodiments 42-51, wherein the compound of formula II is rotigotine sodium salt.

57. The use according to embodiments 42-55 wherein the iontophoresis is anodal and performed at a pH of less than about 6.

58. The use according to embodiments 42-55 or 56 wherein the iontophoresis is cathodal and performed at a pH of at least about 7.5.

59. An iontophoretic system for the delivery of a compound through skin, comprising (a) a transdermal delivery device attachable to the skin, the device including a first electrode and a second electrode, and a reservoir containing a compound of general formula I or a formulation thereof and optionally a pharmaceutically acceptable electrolyte in electrical communication with the first and second electrodes and (b) means for connecting an electrical power source to the first and second electrodes and (c) optionally a membrane closing the reservoir.

60. The iontophoretic system of embodiment 59, wherein the compound is rotigotine dihydrophosphate.

61. The iontophoretic system of embodiment 59, wherein the compound is rotigotine orotate.

62. The iontophoretic system of embodiment 59, wherein the compound is rotigotine hydrogen sulphate.

63. A method for the treatment or the prevention of CNS disorders like Parkinson Disease, fibromyalgia, restless leg syndrome, depression and/or Parkinson's accessory symptoms, characterised by applying an iontophoretic device, which comprises a composition comprising a compound of general formula I and optionally at least one electrolyte, the composition having a pH of less than 6 with the proviso that the compound of general formula I is not rotigotine hydrochloride, onto the skin of a patient in need thereof.

64. A method for administering a pharmaceutically acceptable rotigotine salt of formula I and/or formula (II) to a patient comprising iontophoretically administering to the body surface of a patient in need thereof, the formulation of any one of embodiments 1 to 27.

EXAMPLES

In order to compare the maximum solubility of pharmaceutically acceptable salts of rotigotine, e.g. rotigotine.$H_3PO_4$, with rotigotine.HCl, the solubility studies of rotigotine.salts were carried out as described by Nugroho et al. (Pharm. Res. 21 (2004), 844-855), which is incorporated herein by reference, who determined the solubility of rotigotine.HCl. Briefly, rotigotine.salt was solubilized in 10 mM citric buffer at pH 4, 5 and 6 with and without the presence of NaCl (at room temperature). Subsequent adjustment of pH in each test tube was performed by alternating adding small quantities of 1M NaOH under continuous shaking and subsequent pH measurements, until the pH of each solution had stabilized at the original buffer value. Each solution was shaken for an additional 48 hours, after which each solution was centrifuged and filtered. The concentration in each solution was determined by HPLC. Room temperature or ambient as used in the present application is to be understood to apply to a range from 18° C. to 25° C., preferred is about 20° C.

The preparation of human stratum corneum (HSC) was performed according to the method described previously (Nugroho et al., (Nugroho et al., J. Control Release (2005) 103, 393-403) which is incorporated herein by reference. Briefly, within 24 hours after surgical removal of the human skin residual subcutaneous fat was removed. Dermatomed human skin (DHS) was obtained by dermatoming the skin to a thickness of about 300 μm. In order to obtain HSC, DHS was incubated with the dermal side on Whatman paper soaked in a solution of 0.1% trypsin in 150 mM phosphate buffered saline (PBS) pH 7.4 (NaCl: 8 g·$L^{-1}$, $Na_2HPO_4$: 2.86 g·$L^{-1}$, $KH_2PO4$: 0.2 g·$L^{-1}$, KCl: 0.19 g·$L^{-1}$) overnight at 4° C. and subsequently for 1 hour at 37° C. after which HSC was peeled off from the underlying viable epidermis and dermis. HSC was subsequently washed in a 0.1% trypsin inhibitor solution in Millipore water and several times in water and stored in a desiccator in a $N_2$ environment.

The in vitro transport studies were done by using a 9-channel computer controlled power supply in order to provide a constant direct current (Electronics Department, Gorlaeus Laboratories, Leiden University, The Netherlands) during iontophoresis. The system was equipped with differential input channels per current source enabling on-line measurement of the electric resistance across HSC in each diffusion cell. Ag/AgCl was used as driver electrode pair. All transport experiments were carried out, using a three chamber continuous flow through cell as described elsewhere (Nugroho et al., J. Control Release (2005) 103, 393-403). The donor formulation, buffered with a 10 mM citric buffer, was applied at the anodal side. The cathodal chamber was filled with PBS pH 7.4. The acceptor phase, maintained at 32° C., was continuously perfused with PBS pH 6.2 (NaCl: 8 g·$L^{-1}$, KCl: 0.19 g·$L^{-1}$, $Na_2HPO_4$.$2H_2O$: 0.43 g·$L^{-1}$, $KH_2PO_4$: 0.97 g·$L^{-1}$) at a flow rate of 7.0 ml·$h^{-1}$. Unless described elsewhere, the following protocol for the iontophoresis experiments was used: 6 hours of passive diffusion, followed by 9 hours of iontophoresis with a current density of 500 μA·$cm^{-2}$ and 5 hours of passive diffusion. Samples were collected every hour with an automatic fraction collector (ISCORetriever IV, Beun De Ronde B V, Abcoude, The Netherlands). The specific conditions of the individual transport studies are described below.

Analytical Method

Prior to and at the end of a transport study the pH of donor and acceptor compartment was measured. All samples of the iontophoretic transport studies were analyzed by RP-HPLC using a Superspher® 60 RP-select B, 75 mm-4 mm column (Merck KGaA, Darmstadt, Germany). Rotigotine was detected using a scanning fluorescence detector (Waters™ 474, Millipore, Milford, Mass., USA) at excitation and emission wavelengths of 276 and 302 nm. Acetaminophen was detected using a UV detector (Dual λ Absorbance Detector 2487, Waters, Milford, USA) at a wavelength of 254 nm. Filtered and degassed mobile phase contained 60% $H_2O$ (v/v), 40% ACN (v/v) and 0.05% methanesulfonic acid (v/v). The injection volume was 50 μL and the flow rate was set to 1.0 mL·$min^{-1}$.

The concentration of rotigotine was quantified according to 3 standards with a concentration of 0.005, 2 and 5 μg·$mL^{-1}$. The intra-assay variation of the retention time and of the area was less then 2.0%. For acetaminophen, calibration curves showed a linear response when using concentrations of compounds between 0.1 and 40 μg·$mL^{-1}$ ($r^2$>0.9999). The limit of detection (LOD) and limit of quantification (LOQ) of acetaminophen were experimentally determined at 5.8 and 9.6 ng·$mL^{-1}$ respectively. According to literature the limit of detection of rotigotine (base) was 11 ng·$mL^{-1}$ [2].

Data Analysis

To calculate the steady state flux during passive and iontophoretic transport, the cumulative flux of the transport was plotted as a function of time. The steady state flux was estimated from the linear part of the slope of this plot according to the permeation lag-time method[7]. All data are presented as mean±standard deviation (s.d.). When a statistical analysis was performed comparing only 2 groups, a Students t-test was used. When 3 or more groups were compared, a 1-way ANOVA statistical analysis was executed. If the overall p-value was less than 0.05, a bonferonni post-test was applied to compare different groups. For all statistical analysis a significance level of p<0.05 was used.

Example 1

Solubility of Rotigotine Hydrophosphate and Rotigotine Hydrochloride

The maximum solubilities of rotigotine hydrochloride (abbreviated as Ro.HCl) and rotigotine hydrophosphate (abbreviated as rotigotine.$H_3PO_4$ or Ro.$H_3PO_4$) have been investigated as a function of pH in a number of solvents (table.1). Ro.$H_3PO_4$ was dissolved in the indicated buffer upon which the pH of the formed solution was adjusted to the target value by addition of sodium hydroxide solution. During addition rotigotine precipitated indicating that saturation was achieved. The drug was assayed by HPLC analysis in the filtered solution.

HPLC Conditions:

Column: Merck Superspher 60 RP select B, length: 7.5 cm, column internal diameter: 4 mm, particle size: 5 μm Mobile phase: 60% (v/v) water, 40% (v/v) acetonitrile 0.05% (v/v) methanesulfonic acid Flow: 1.0 ml/min Injection volume: collected fractions: 50 μl, diluted donor solutions: 4 μl Column temperature: ambient Detection: fluorescence, $\lambda_{ex}$=276 nm, $\lambda_{em}$=302 nm

TABLE 1

The solubility of Rotigotine•H$_3$PO$_4$ and Rotigotine•HCl in different medium at pH 4, 5 and 6 in the presence and absence of 68 mM NaCl (n = 2-3).

| pH | Solubility of Rotigotine•H$_3$PO$_4$ (μmol/ml) | | Solubility of Rotigotine•HCl (μmol/ml) | |
|---|---|---|---|---|
| | No NaCl | 68 mM NaCl | No NaCl | 68 mM NaCl |
| 4 | 83.48$^a$ | 80.08$^c$ | 24.39$^{a,b}$ | 6.75 |
| 5 | 41.89$^a$ | 42.95$^c$ | 22.45$^{a,b}$ | 6.35 |
| 6 | 15.67 | 14.44$^d$ | 15.87$^b$ | 6.52 |

$^a$p < 0.001;
$^b$p < 0.001;
$^c$p < 0.001;
$^d$p < 0.01
*the values were adapted from reference (Nugroho et al.)

As shown in table 1, in the presence of NaCl in the donor formulation, the solubility of rotigotine increased substantially when HCl was replaced by H$_3$PO$_4$.

At the selected pH values the addition of NaCl did not affect significantly the solubility of rotigotine.H$_3$PO$_4$ (2-way ANOVA; p>0.05), which contrasted the results obtained with rotigotine.HCl by Nugroho. For rotigotine.HCl the solubility reduced tremendously after adding 68 mM NaCl. The pH had a drastic influence on the solubility of rotigotine.H$_3$PO$_4$. Decreasing the pH of the donor phase from 6 to 5 and again to pH 4 resulted in a significant increase in the solubility of rotigotine (2-way ANOVA; p<0.05). Compared to rotigotine-HCl the solubility of rotigotine.H$_3$PO$_4$ is 2, 7, 12 fold higher at pH 6, 5 and 4, respectively. Furthermore in contrast to the solubility of the HCl-salt the presence of NaCl did not affect the solubility of rotigotine.H$_3$PO$_4$.

Example 2

Iontophoresis Experiments

Many of the experiments were performed under the following test conditions—the standard conditions (If not stated otherwise these ones have been used in the respective examples):

Donor solvent: citrate buffer (10 mM citrate, see Table 2), 4 g/l NaCl and 23 g/l mannitol, pH as indicated per experiment.

TABLE 2

Concentrations for producing citrate buffers at the indicated pH, other components, see above.

| | Concentration (g/l) | |
|---|---|---|
| pH | citric acid•H$_2$O | trisodium citrate•2H$_2$O |
| 5.0 | 0.73 | 1.94 |
| 5.5 | 0.46 | 2.30 |
| 6.0 | 0.24 | 2.60 |

Donor liquid preparation: a quantity of rotigotine.H$_3$PO$_4$ is dissolved in the indicated donor solvent to produce a sufficient amount of donor liquid at the selected concentration. The pH of the formed solution is adjusted to the target value by addition of sodium hydroxyde solution. The solution is then filtered over a membrane filter (pore size: 0.45 μm) and diluted with the same donor solvent as required to produce a concentrated drug solution of the indicated concentration.

Acceptor liquid: PBS pH=6.2:0.965 g/l KH$_2$PO$_4$, 0.425 g/l Na$_2$HPO$_4$.2H$_2$O, 8 g/l NaCl, 0.19 g/l KCl Kathode liquid: PBS pH=7.4, 0.19 g/l KH$_2$PO$_4$, 1.44 g/l Na$_2$HPO$_4$.2H$_2$O, 8 g/l NaCl, 0.19 g/l KCl Flow acceptor liquid: 6.5 ml/h Temperature circulating water bath: 37° C.

Iontophoresis protocol: 6 hours: no current, 9 hours: 500 μA/cm$^2$, 5 hours: no current.

Steady state flux calculation: the mean from flux values recorded within the time interval within which each flux value deviates not more than 10% from that mean.

The iontophoresis cells used in the studies is a three compartment cell. A exemplarily design of cell is provided in FIG. 1.

The cell as shown in FIG. 1 consists of three compartments. An anodal (+electrode) and cathodal (−electrode) compartment in which the Ag and AgCl electrode, respectively, are located. In the donor (anodal) compartment the positively charged drug rotigotine is dissolved in the buffer solution. In between the anodal and cathodal compartment a third compartment is located. During an iontophoresis experiment a constant flow of buffer is transport across this compartment simulating the blood flow in vivo. On both sides of the central compartment human skin is clamped (between anodal-acceptor compartments and cathodal-acceptor compartments). The skin is clamped in such a way the inner part of the skin or stratum corneum is facing the acceptor compartment. In this way the in vivo situation is closely simulated.

Some of these conditions were varied in the experiments in order to study the impact of their variation on the drug flux.

As stated below a series of iontophoretic transport studies under various conditions were performed to investigate the iontophoretic delivery of rotigotine.H$_3$PO$_4$. During 6 hours prior to iontophoresis no current was applied and passive transport of rotigotine was observed, which reached steady state conditions within this period of 6 hours. From the slope of the linear part of the cumulative flux vs time profile the passive steady state (Flux$_{pss}$) was calculated. The influence of the pH of the donor solution on the passive transport of rotigotine.H$_3$PO$_4$ was investigated. The results of transport studies at various donor concentrations, comparing a donor pH of 5 and 6 are depicted in FIG. 4. A non-linear hyperbolic fit showed a correlation between the Flux$_{pss}$ and the donor concentration for pH 5 ($R^2$=0.889). Increasing the pH of the donor phase from 5 to 6 increased the passive flux of rotigotine.H$_3$PO$_4$ quite drastically: Close to saturation of rotogotine.H$_3$PO$_4$ in the donor phase the maximum flux that could be achieved was 10.8±1.9 nmol·cm$^{-2}$·h$^{-1}$ at pH 5 and 24.9 nmol·cm$^{-2}$·h$^{-1}$±2.5 at pH 6.

A series of iontophoretic transport studies was conducted to investigate the iontophoretic transport of rotigotine.H$_3$PO$_4$ under various conditions specially focusing on (i) the relationship between the flux and donor concentration, (ii) the influence of the pH, (iii) the determination of the transport number, (iv) impact of current density, (v) impact of chloride salt, (vi) in vivo simulation.

(i) Impact of Donor Concentration

In these transport studies 4 different concentrations rotigotine.H$_3$PO$_4$ (4.4 mM, 9.5 mM, 22.2 mM and 47.5 mM (corresponding to concentrations rotigotine free base of 1.4 mg/ml, 3 mg/l, 7 mg/ml and 15 mg/ml), buffered at pH 5, were used. All transport experiments were performed in the presence of 68 mM NaCl in the donor phase.

TABLE 3

Drug concentration in donor phase versus steady state flux values, conditions: pH = 5.0, other conditions, see text.

| Rotigotine free base conc. (mg/ml) | Mean steady state flux ± sd (µg/cm²/h) |
|---|---|
| 1.4 | 22.1 ± 2.5 |
| 3 | 26.0 ± 2.1 |
| 7 | 37.7 ± 1.5 |
| 15 | 41.5 ± 3.4 |

Note:
mean values from 4 experiments, concentrations in this table are nominal, actual assayed drug concentration vary per experiment.

The highest drug concentrations in this graph of FIG. 2 represent 80% of the maximum solubility of rotigotine.H$_3$PO$_4$ at pH=5.0.

The linear relationship between drug concentration in the range 0.5 to 1.4 mg/ml and steady state flux observed earlier for rotigotine.HCl is no longer present in the higher concentrated range between 1.4 and 15 mg/ml. Instead, increasing drug concentration from 7 to 15 mg/ml increases the flux only from 38 to 41 µg/cm²/h.

As shown in FIG. 3, current application results in an immediate increase in the flux of rotigotine.H$_3$PO$_4$, which reaches steady state within four hours. The results of a series of iontophoretic transport studies of different concentrations rotigotine.H$_3$PO$_4$ varying from 4.4 mM to 47.5 mM at pH 5 and 4.4, 13.5 mM (millimolar) at pH 6 are depicted in FIGS. 2 and 4. A non-linear relationship can be described between the Flux and the donor concentration at pH 5 ($R^2$=0.825). Thereby the Flux$_{ss}$ at equal rotigotine.H$_3$PO$_4$ concentration increases with increasing pH of the donor solution.

(ii) Impact of pH

Further to the under (i) mentioned transport studies at 4 different concentrations rotigotine.H$_3$PO$_4$ (4.4 mM, 9.5 mM, 22.2 mM and 47.5 mM), buffered at pH 5, the transport of rotigotine.H$_3$PO$_4$ (4.4 and 13.0 mM), buffered at pH 6 was investigated as well. All transport experiments were performed in the presence of 68 mM NaCl in the donor phase.

However, when comparing the Flux$_{ss}$ at pH 5 and 6 close to saturation in the donor phase, the Flux$_{ss}$ values are very similar as shown in FIG. 4.

Experiments have been performed to study the effect of pH and donor concentration on both passive and iontophoretic drug flux. Acceptor solvent pH (=6.2) is the same for all experiments. The table 4 and FIG. 5 summarise the impact of pH and drug concentration on steady state flux of rotigotine during the passive and active stage of a number of experiments.

TABLE 4

Impact of pH value donor solution on passive and iontophoretic transdermal rotigotine flux (calculated as free base).

| pH | rotigotine free base donor conc. ± s.d. (mg/ml) | steady state flux ± s.d. (µg/cm²/h) | |
|---|---|---|---|
| | | passive stage | iontophoresis stage |
| 5.0 | 1.28 ± 0.03 | 0.5 ± 0.2 | 20.0 ± 4.9 |
| | 1.46 ± 0.04 | 0.9 ± 0.3 | 22.1 ± 2.5 |
| | 3.11 ± 0.16 | 1.0 ± 0.1 | 26.0 ± 2.1 |
| | 6.95 ± 0.23 | 2.3 ± 0.5 | 33.7 ± 4.7 |
| | 15.09 ± 0.30 | 3.6 ± 0.5 | 41.5 ± 3.4 |
| 5.5 | 9.88 | 7.7 ± 0.5 | 47.9 ± 3.1 |
| 6.0 | 1.24 | 4.1 ± 1.9 | 26.4 ± 1.3 |
| | 1.42 | 3.2 ± 0.2 | 25.1 ± 3.3 |

TABLE 4-continued

Impact of pH value donor solution on passive and iontophoretic transdermal rotigotine flux (calculated as free base).

| pH | rotigotine free base donor conc. ± s.d. (mg/ml) | steady state flux ± s.d. (µg/cm²/h) | |
|---|---|---|---|
| | | passive stage | iontophoresis stage |
| | 4.13 ± 0.14 | 9.3 ± 0.9 | 43.0 ± 2.6 |
| | 4.3 | 12.3 ± 0.9 | 47.1 ± 1.8 |

As can bee seen the highest tested rotigotine concentrations at pH 5.0, 5.5 and 6.0 are approximately 4, 10 and 15 mg/ml, which is 90% (pH=5.0 and 5.5) or 80% (pH=6.0) of the maximum solubility of the acid addition salt of rotigotine, e.g. rotigotine.H$_3$PO$_4$ at that pH value.

(iii) Determination of Transport Number

In a single experiment the relationship between the Flux$_{ss}$ and the current density was studied with a donor solution, buffered at pH 5.5, containing 31.3 mM rotigotine.H$_3$PO$_4$ in the presence of 68 mM NaCl. The following protocol was used: 6 h passive+6 h 166 µA·cm$^{-2}$+6 h 333 µA·cm$^{-2}$+6 h 500 µA·cm$^{-2}$+6 h passive. The donor concentration was 90% of the maximum solubility of rotigotine.H$_3$PO$_4$ under these conditions. An increase in the current density resulted in a significant increase in flux, which reached steady state within 6 hours of current application. A current density of 0 µA·cm$^{-2}$ (passive phase), 166 µA·cm$^{-2}$, 333 µA·cm$^2$ and 500 µA·cm$^{-2}$ resulted in a Flux of 24.4±1.9 nmol·cm$^{-2}$·h$^{-1}$, 65.8±9.3 nmol·cm$^{-2}$·h$^{-1}$, 109.7±15.7 nmol·cm$^{-2}$·h$^{-1}$ and 154.5±27.0 nmol·cm$^{-2}$·h$^{-1}$, respectively. An excellent linear correlation could be observed between the Flux$_{ss}$ and the current density ($R^2$=0.999) and the transport number was calculated from the slope of the correlation at 0.7%. The transport number of rotigotine.H$_3$PO$_4$ at pH 5.5 in the presence of 68 mM NaCl was estimated from the slope of relationship between the Flux$_{ss}$ and the current density at 0.7%, which is higher than the transport number of rotigotine.HCl (0.4%) at pH 5, which can be explained by a higher donor concentration of rotigotine.H$_3$PO$_4$ (iv) Impact of Current Density The current density was varied over the time of the experiment according to the following: 0-6 hours: no current; 6-12 hours: 167 µA/cm$^2$; 12-18 hours: 333 µA/cm$^2$; 18-24 hours: 500 µA/cm$^2$; 24-30 hours: no current.

Protocol a: The impact of iontophoretic current density on the drug steady state flux has been examined with drug donor concentration (calculated as free base) 7 mg/ml and pH=5.0. Per experiment three current density values were tested with two cells per current value.

Protocol b: The impact of iontophoretic current density on the drug steady state flux has been examined at pH=5.5, drug donor concentration (calculated as free base): 9.9 mg/ml (31.3 mM) (=90% of maximum solubility at pH=5.5). Per experiment three current density values were tested with two cells per current value. Results are summarized in Table 5.

TABLE 5

Iontophoretic steady state flux at various current density values, drug conc.: 7 mg/ml (protocol a) and 9.9 mg/ml (protocol b).

| current density (µA/cm²) | rotigotine flux$_{ss}$ ± sd (µg/cm²/h) | |
|---|---|---|
| | Protocol 1 (pH = 5.0) | Protocol 2 (pH = 5.5) |
| 167 | 12.3 ± 0.3 | 20.2 ± 2.3 |
| 333 | 21.0 ± 1.1 | 33.8 ± 2.9 |
| 500 | 29.7 ± 0.5 | 47.7 ± 3.1 |

From these results as shown in FIG. 6 it can be concluded that there is a linear relationship between applied current density and transdermal rotigotine flux at both pH values and concentration levels. Also with no current switched on there is a drug flux which represents the passive diffusion level. Changing the current density rapidly changes the rotigotine flux in a predictable way and therefore the flux can be adjusted to the requirements of the individual patient.

The relationship between the current density was further studied with a rotigotine.$H_3PO_4$ concentration of 31.3 mM, buffered with a citric buffer at pH 5.5, containing 68 mM NaCl. The following protocol was used: 6 h passive+6 h 166 $\mu A \cdot cm^{-2}$+6 h 333 $\mu A \cdot cm^{-2}$+6 h 500 $\mu A \cdot cm^{-2}$+6 h passive.

(v) Impact of Sodium Chloride

As shown by table 1 sodium chloride has no negative impact on rotigotine phosphate solubility and can thus be added to the donor solution to feed the electrochemical reaction at the anodal side.

(Vi) In Vivo Simulation

After characterizing and optimizing the transdermal delivery of this promising compound in vitro, the potential of the iontophoretic delivery of rotigotine in vivo was evaluated in a series of simulations, using pharmacokinetic modeling. The first step was to determine the parameters driving the iontophoretic delivery in vitro across human stratum corneum of rotigotine.$H_3PO_4$ (47 mM), buffered at pH 5. The value of the $Flux_{ss}$ corresponds well with the value estimated by the permeation lag time method. In addition diagnostic plots of the data modeling confirm that this model successfully describes the in vitro iontophoretic transport of rotigotine.$H_3PO_4$. In the next step the apparent pharmacokinetic parameters of rotigotine reported in literature, are combined with the best-fit values of $Flux_{ss}$, $K_R$ and $t_L$ to predict the plasma levels in vivo. For these simulations 2 different protocols were used to evaluate the iontophoretic delivery of rotigotine (47 mM, pH 5) during 24 h and a comparison was made with the passive delivery of rotigotine. As found in literature, passive delivery of rotigotine with a patch size of 10 $cm^2$, estimated to deliver 2 mg in 24 h, resulted in a maximum plasma concentration ($C_{max}$) of 215 $\mu g \cdot ml^{-1}$ at 16 $h^{21}$. As shown in FIG. 7 applying a current density of 350 $\mu A \cdot cm^{-2}$ during 24 h (protocol 1) is expected to result in $C_{max}$ of 630 $\mu g \cdot ml^{-1}$. Not only can a higher flux be established with iontophoresis, but more interestingly already at time=5 h a plasma concentration of 240 $\mu g \cdot ml^{-1}$ can be reached. Therefore the in vivo iontophoretic delivery of rotigotine was simulated using protocol 2, applying initially a current density of 350 $\mu A \cdot cm^{-2}$ for 5 h, after which the current density was decreased to 150 $\mu A \cdot cm^{-2}$ resulting in a steady state plasma concentration during 19 h. These simulations demonstrate two very important benefits of iontophoretic delivery of rotigotine in combination with iontophoresis over transdermal passive diffusion for symptomatic treatment of Parkinson's disease. Because of active transdermal delivery the onset time to achieve the desired level can be significantly decreased. Secondly by adjusting the current density a titration of the plasma concentration is possible, making it feasible to individually modulate the delivery according to the desired dosing regimen.

CONCLUSION

One advantage is the increase in solubility of rotigotine.$H_3PO_4$ compared to that of rotigotine.HCl, which results in an increase in the maximum iontophoretic transport. At pH 5 the latter resulted in a maximum iontophoretic flux of 80.2±14.4 nmol·$cm^{-2} \cdot h^{-1}$, while with rotigotine.$H_3PO_4$ a maximum flux of 135.8±12.5 nmol·$cm^{-2} \cdot h^{-1}$ was achieved. This means that the maximum flux can be increased with 170% by replacing the HCl salt by $H_3PO_4$. Besides a higher flux another practical advantage can be established when using a high donor concentration at pH 5. Calculations revealed that after 24 h, maintaining a maximum flux of 135.8 nmol·$cm^{-2} \cdot h^{-1}$, the amount rotigotine.$H_3PO_4$ in the donor phase decreased with 35%. This decrease in donor concentration would result only in a decrease of 10% in steady state flux, showing that with a high donor concentration a high flux can be maintained for a long time. Taking these results together, preferably one should seek a balance between transport efficiency and donor concentration by choosing the pH of the donor solution. On one hand by increasing the pH it is possible to increase the transport efficiency, however the limited solubility of the compound at pH 6 prevents the use of a high concentration. On the other hand at pH 5 the transport efficiency is lower, nonetheless a high flux can be established for a long time due to the higher solubility of rotigotine-$H_3PO_4$.

It is clear from the data obtained that rotigotine iontophoresis using rotigotine acid addition salts, in particular rotigotine dihydrogen phosphate, providing a higher saturation solubility of the salt in an aqueous solution than 16 $\mu mol/ml$ at a pH less than 6 and/or a saturation solubility in an aqueous solution of at least 30 $\mu mol/ml$ pH≤5, wherein all the above saturation solubilities are calculated based on the total amount of rotigotine in the pharmaceutically acceptable acid addition salt, is promising.

Fluxes of around 50 $\mu g/cm^2/hr$ can be achieved. A linear relationship between iontophoresis (steady state flux) and current density was obtained, which allows individual dose titration into the patient.

Example 3

General Procedure for Preparation of Rotigotine Acid Addition Salt

Rotigotine free base (6 g) was dissolved in isopropanol (IPA) (24 ml, 4 volumes) at ambient (app. 20° C.) and 800 $\mu l$ was charged to a vial which were capped and stood at ambient for 1.5 hours. The solutions were heated to 60° C. and the acid was added as stock solutions (1 eq. in $H_2O$ or THF depending on solubility). The reaction mixtures were stirred at elevated temperature for 10 minutes and then cooled slowly to ambient. After 2 hours at ambient the reaction mixtures solutions were stored at 4° C. for 16 hours.

Rotigotine Dihydrogen Phosphate Salt (LJC-028-037-1)

Figure 9:
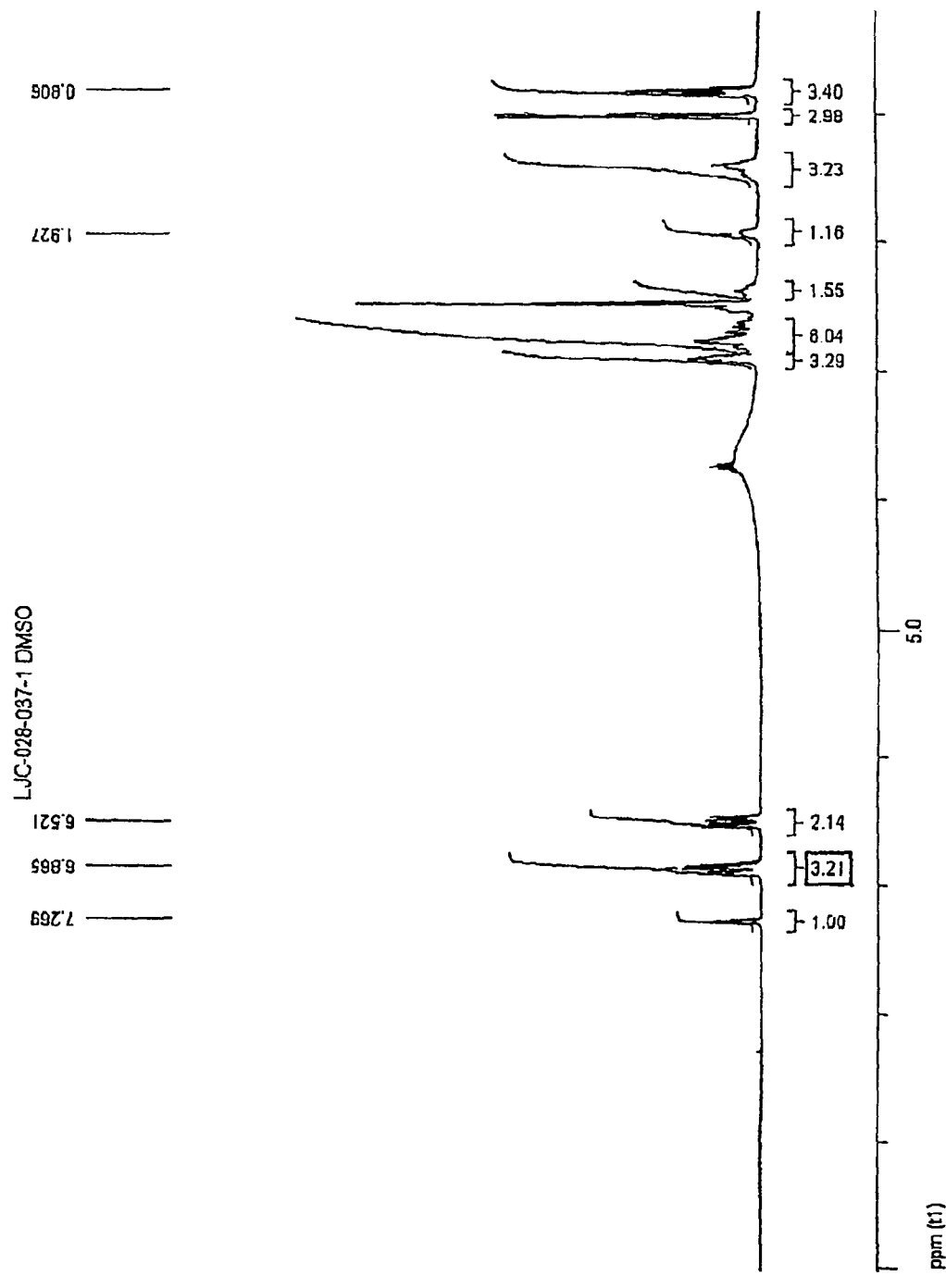
FIG. 9 shows a $^1$H NMR spectra of rotigotine dihydrogen phosphate.

Rotigotine free base (500 mg, 1.58×$10^{-3}$ mol) was charged to a 5 ml round bottomed flask and IPA (1.5 ml, 3 volt) added at ambient. To the solution $H_3PO_4$ (171 mg, 1.1 eq.) was charged as solid and immediately an agglomeration of white material formed. The reaction mixture was stirred for 30 minute at ambient and sonicated in order to break up the ball of material. The powder was stirred for one hour and the solid was filtered and washed. The solid began to deliquesce, so was plunged back into the filtrates, and $H_2O$, (75 $\mu l$) was added. The reaction mixture was heated to 55° C., held for 15 minutes and cooled to ambient. After 12 days standing at ambient without stirring, the yellow solution was decanted from the gum and concentrated under vacuum to yield a white/off-white solid. The material was oven dried at 40° C. under vacuum for 2 hours. A yield of 525 mg was obtained as an amorphous solid and analyzed by XRPD (FIG. 8). The diffractogram can not be defined as reference, because it is amorphous. It is important to realize that in a non-crystalline sample, molecules within that sample would be in random orientations and therefore would have a continuous Fourier spectrum that spreads its amplitude more uniformly and with a much reduced intensity and more importantly, the orientational information is lost. In the crystal, the molecules adopt the same orientation within the crystal, whereas in a liquid, powder or amorphous state, the observed signal is averaged over the possible orientations of the molecules. Therefore the salt was further characterized by $^1$H NMR (FIG. 9) (comprising small amounts of IPA and ultimate analysis (elementary analysis). Carbon and Hydrogen content have been determined by according to DIN51721; phosphor and sulphur have been determined according to DIN EN 1189 (photometric): C 51.3%, H 6.96%, S 6.75%, P 8.17%, all results correspond to calculation. DSC did not provided a clear signal.

Rotigotine Dihydrogen Citrate Salt (LJC-028-037-2)

Figure 10:
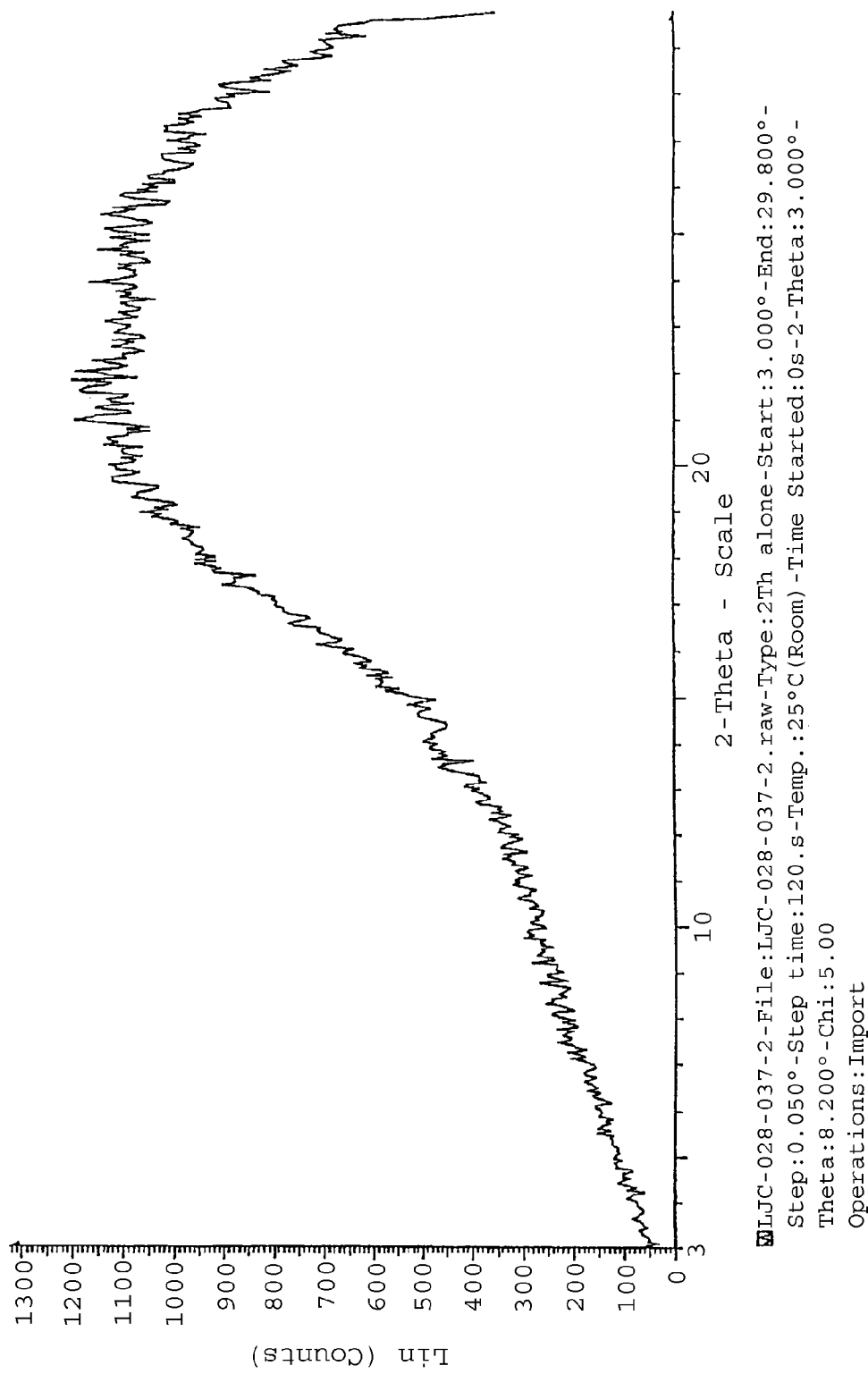
FIG. 10 shows a XRPD of rotigotine dihydrogen citrate
Figure 11:
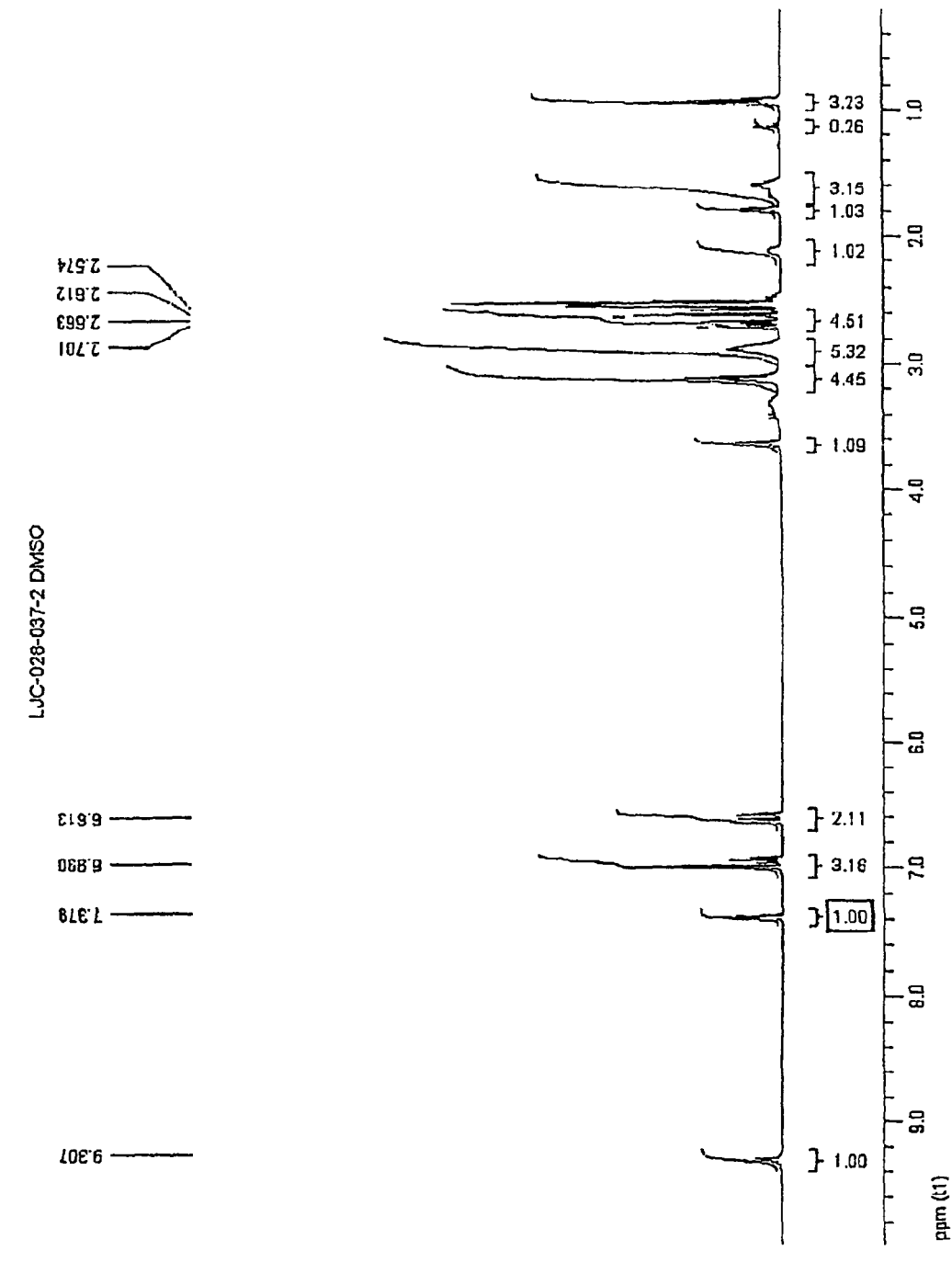
FIG. 11 shows a $^1$H NMR spectra of rotigotine dihydrogen citrate.

Citric acid (1.74 ml, 1 equ, 1 M in THF) was charged to a 5 ml round bottomed flask and rotigotine free base (500 mg, 1.58 mg×10$^{-3}$ mol) was added in portions. An orange agglomeration of material formed which prevented stirring. After manual shaking most of the gelatinous material had dissolved in the THF, but stirring was still difficult. H$_2$O (87 µl) was added, and the reaction mixture was heated to 50° C. for 5 minutes, then slowly cooled to 40°. At this temperature heptane (5×200 µl) was added and no cloud point was obtained, so the reaction mixture was cooled to ambient. An oily gum formed after 16 hours, which was triturated with Et$_2$O and stored at –20° C. for a further 16 hours. The solvent was decanted and the gum brought to ambient then tritiuration was carried out with n-heptane, n-pentane, MtBE and Et$_2$O. Solid did not materialise. The gum was stood at ambient for 9 days and it slowly began to solidify as an amorphous solid and analyzed by XRPD (FIG. 10) The salt was further characterized by 1H NMR (FIG. 11).

Rotigotine Hydrogen L-Tartrate Salt (LJC-028-050-1)

Figure 12:
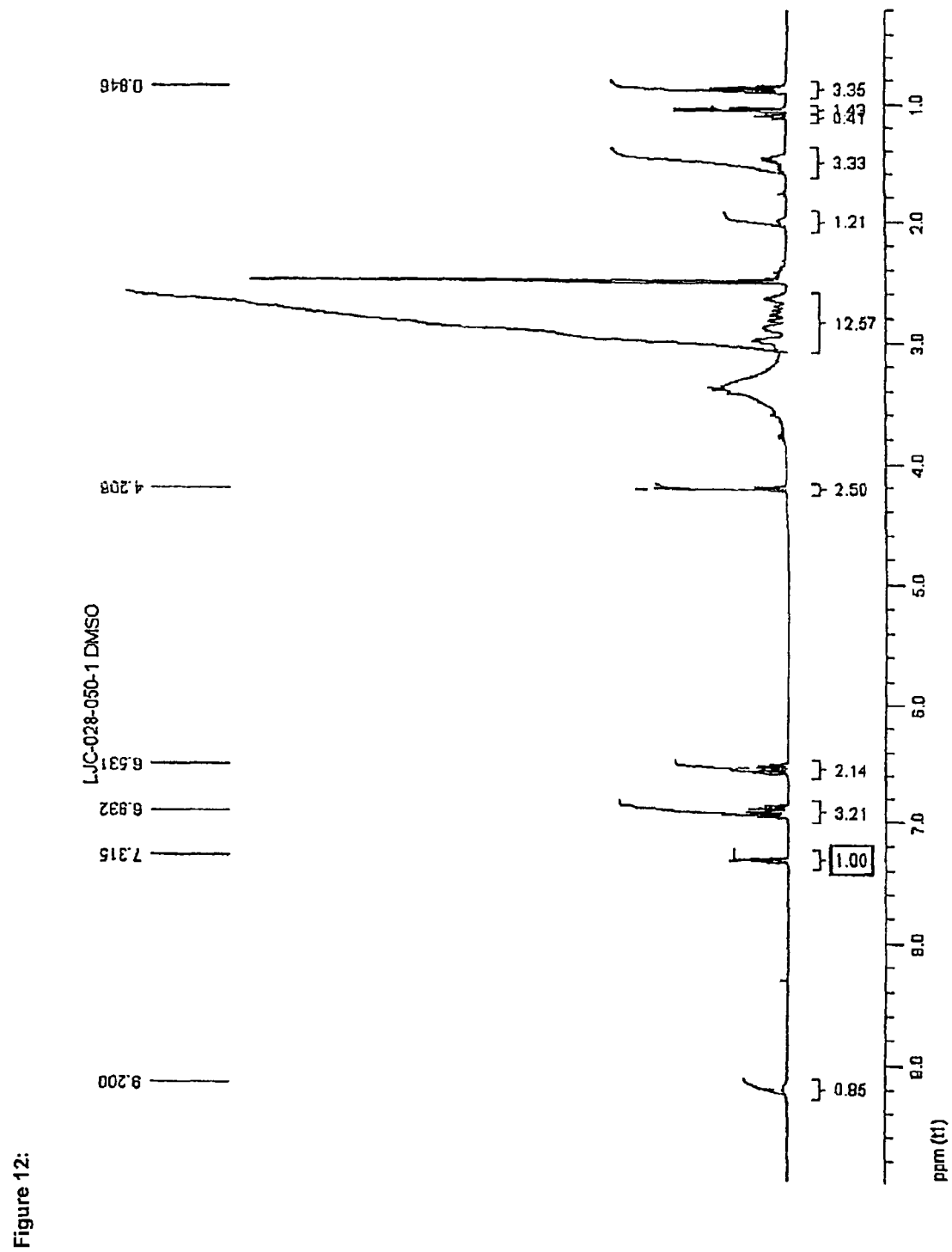
FIG. 12 shows a $^1$H NMR spectra of rotigotine hydrogen tartrate.

Rotigotine free base (100 mg, 3.17×10$^{-4}$ mol) was charged to a vial and IPA (300 µl, 3 vol) was added at ambient. The solution was then heated to 60° C. and L-tartaric acid (630 µl, 1M, in THF) was added and the solution held at the elevated temperature for 10 minutes. The heat was removed and the solution cooled slowly. No precipitate had formed so the solution was stored at 4° C. for 16 hours. After 10 days the solution was concentrated under vacuum to an oil which was triturated with Et$_2$O. The oil solidified and was confirmed as the tartrate salt by $^1$H NMR (FIG. 12).

Rotigotine Orotate Salt (LJC-028-045-2)

Figure 13:
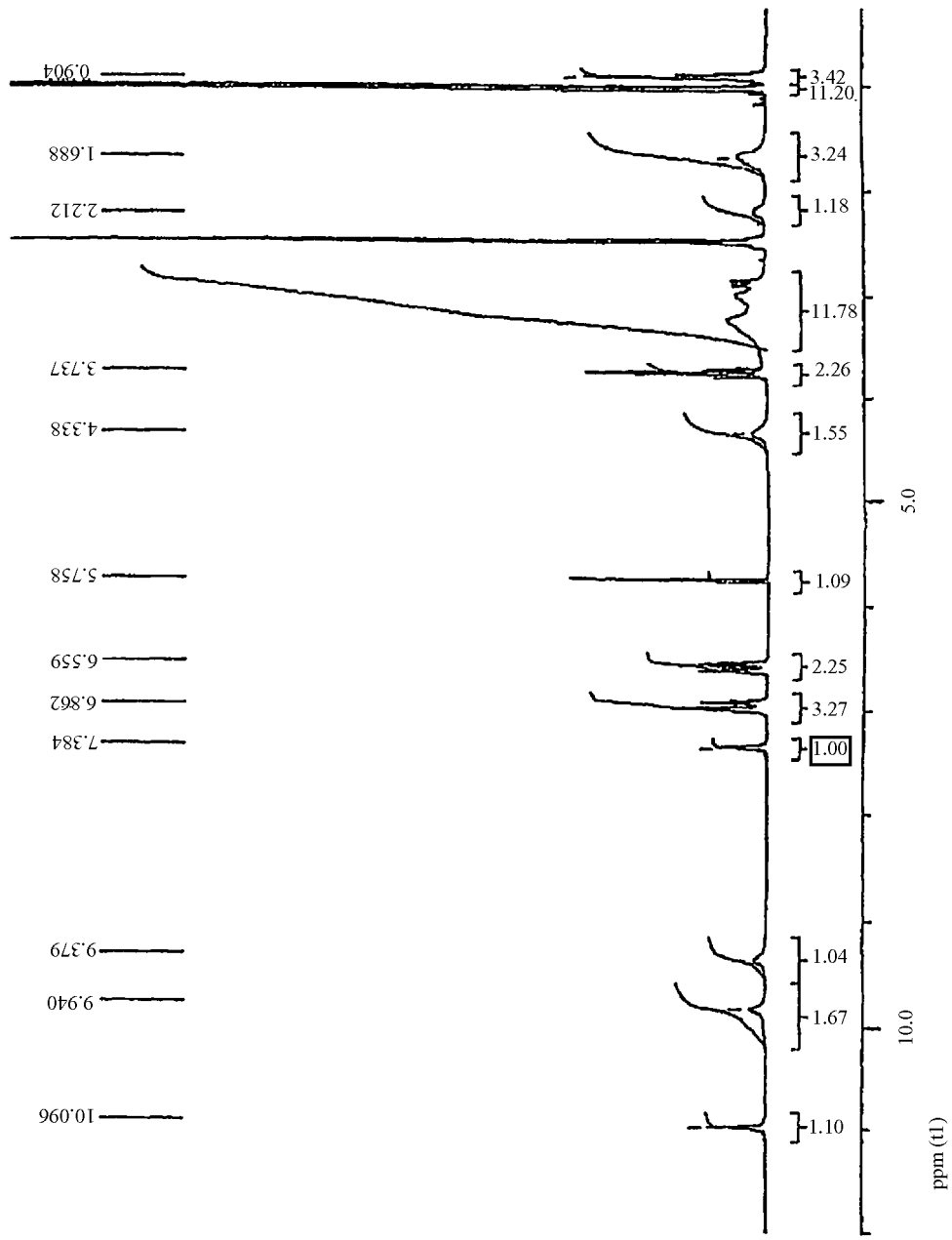
FIG. 13 shows a $^1$H NMR spectra of rotigotine orotate.

Rotigotine free base (1.0 g, 3.170×10-3 mol) was charged to a 25 ml round bottomed flask and IPA (4 ml) added. The reaction mixture was stirred until all solid had dissolved and orotic acid (490 mg, 1 equ) was added as a solid. The suspension was stirred at ambient for 10 minutes and then heated to 75° C. Some material had dissolved, but it was not a complete solution. After 10 minutes at 75° C., the heat was turned off and the reaction mixture cooled slowly at 10° C. an hour. Once at 55° C., the reaction mixture was aged for 16 hours. The reaction mixture was then cooled to ambient, where a mixture of powder and very hard solid was present. The powder was filtered and the hard material was manually broken up then filtered. The solid was washed in IPA and dried at 40° C. under vacuum. $^1$H NMR confirmed the orotate salt (FIG. 13).

Figure 14:
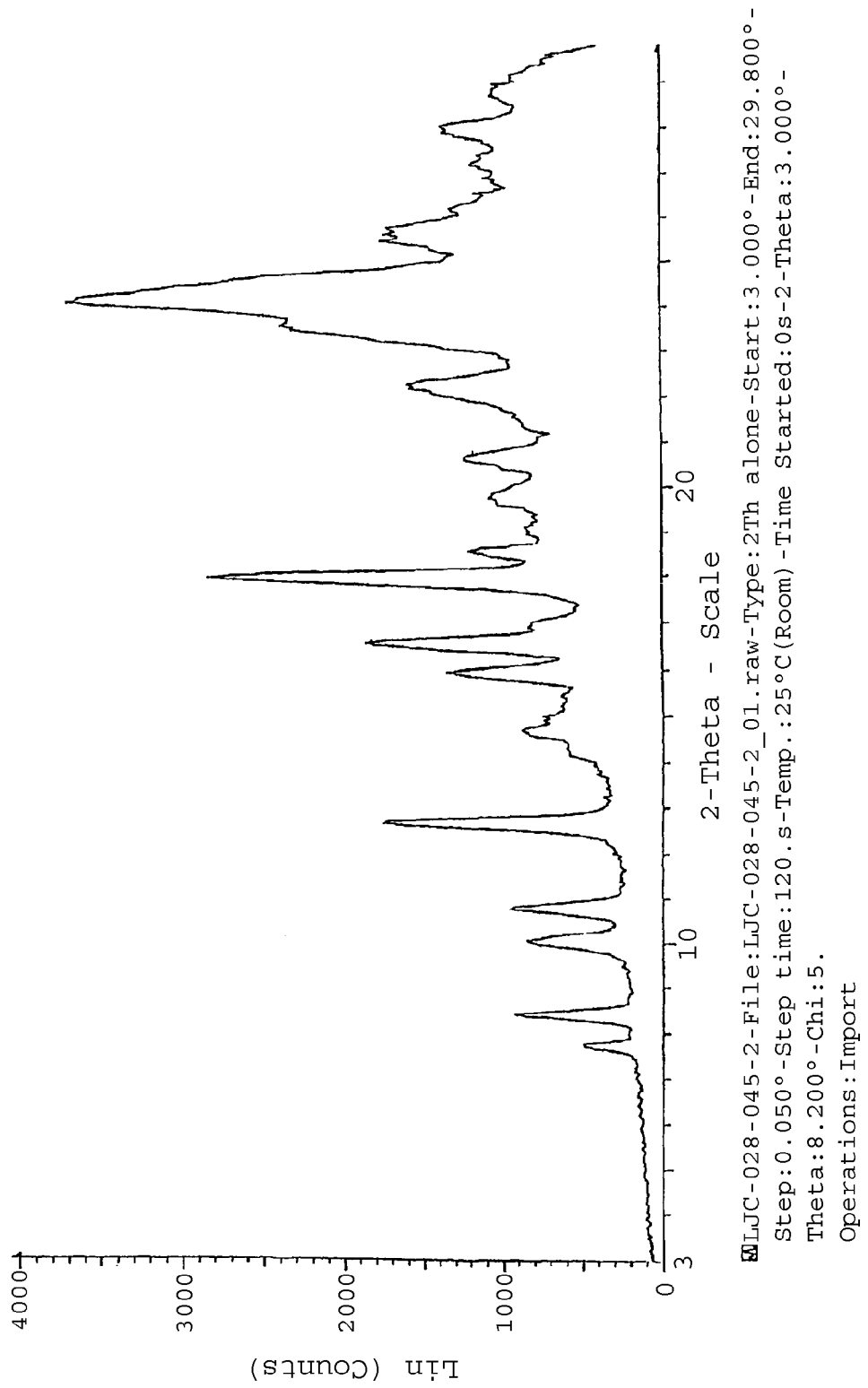
FIG. 14 shows a XRPD of rotigotine orotate.

This orotate salt (≈75 mg) was charged to a vial and slurried in iPrOAc (10 vol) on a double heat/cool cycle from 25° C. to 50° C. The vial was shaken over the 48 hour period and then filtered, washed and dried at 40° C. under vacuum. XRPD confirmed crystalline material (FIG. 14).

Rotigotine 1-hydroxy-2-naphtoate Salt (LJC-028-020-1)

Figure 15:
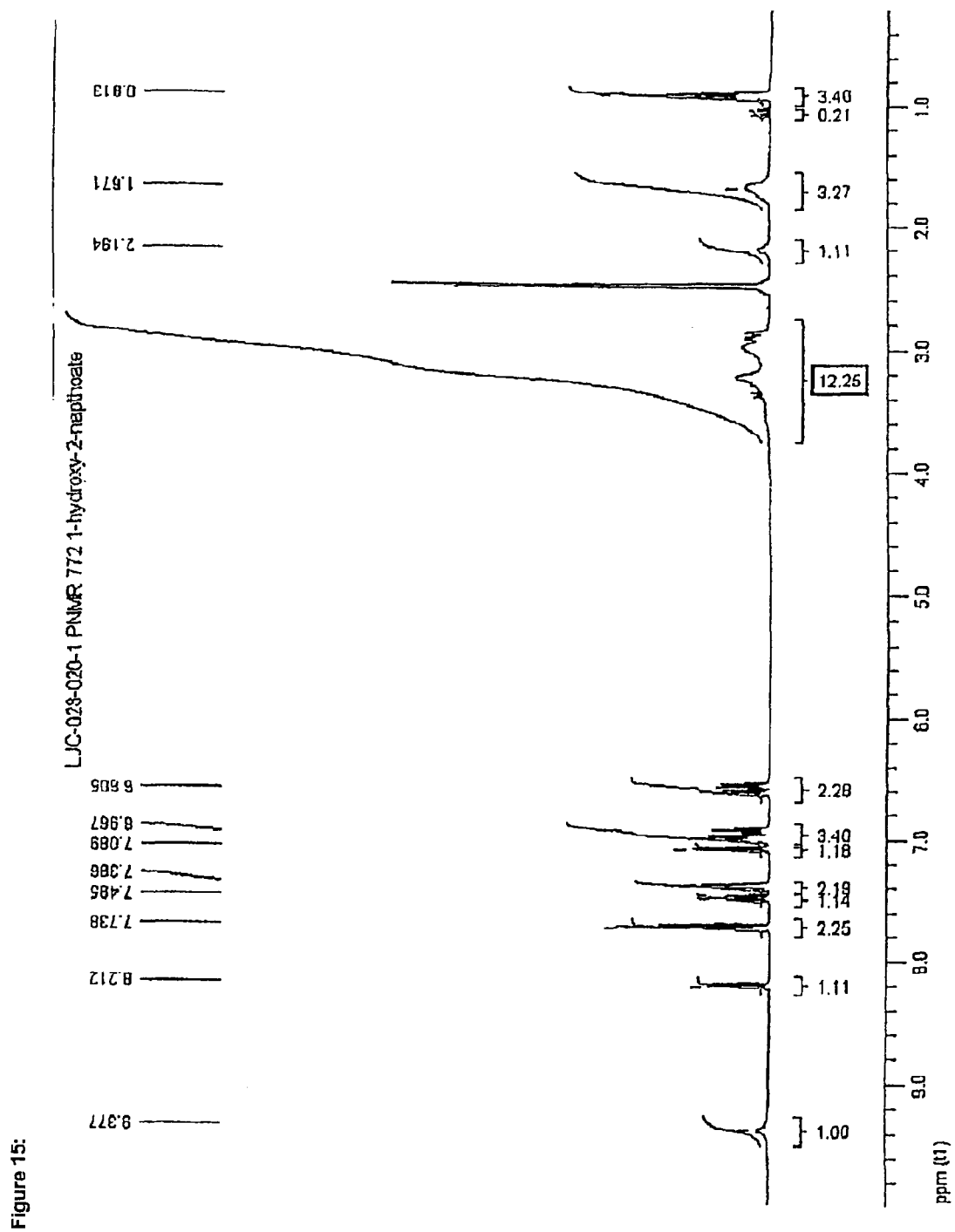
FIG. 15 shows a $^1$H NMR spectra of rotigotine 1-hydroxy-2-naphtoate
Figure 16:
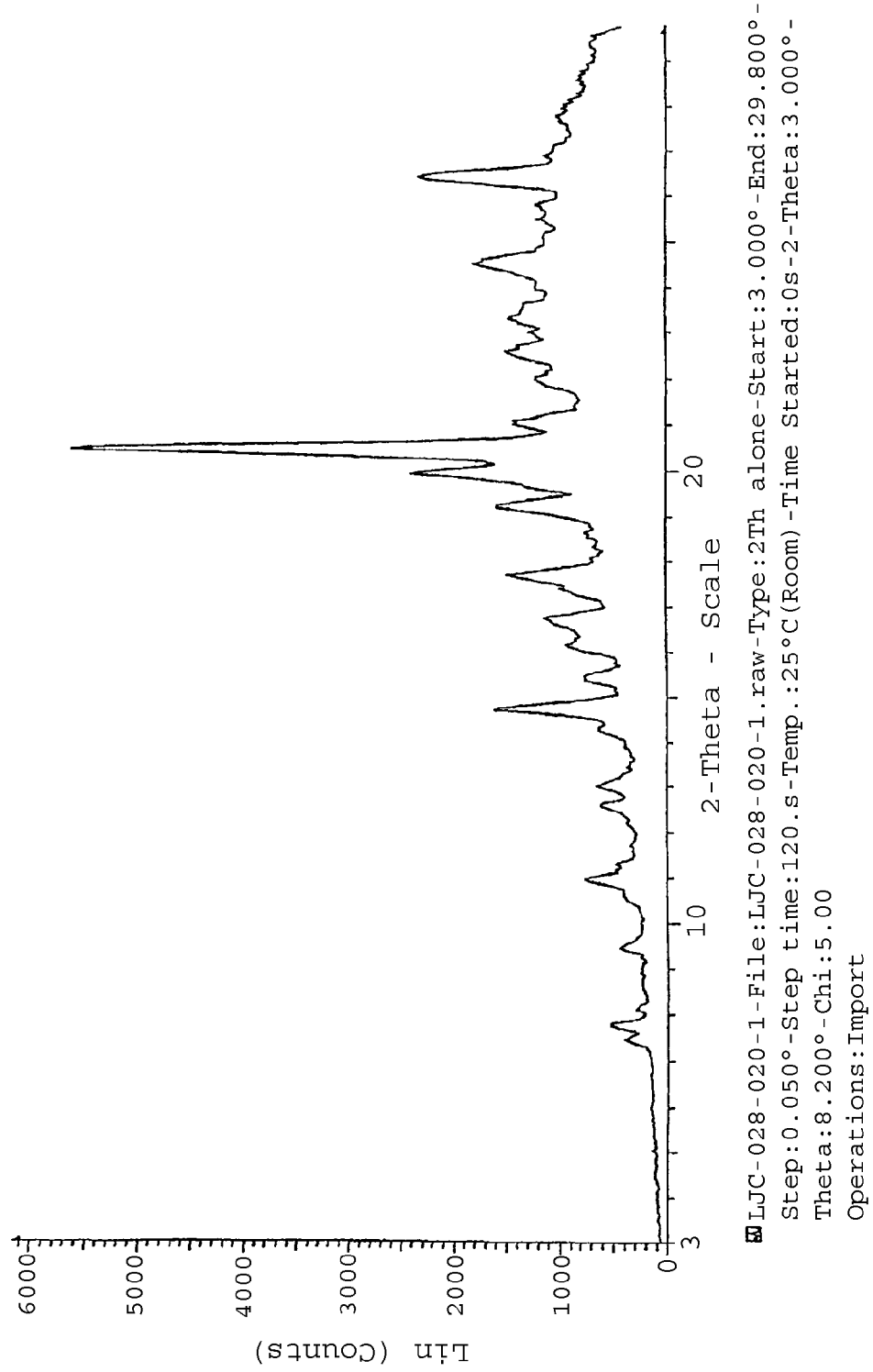
FIG. 16 shows a XRPD of rotigotine 1-hydroxy-2-naphtoate
Figure 17:
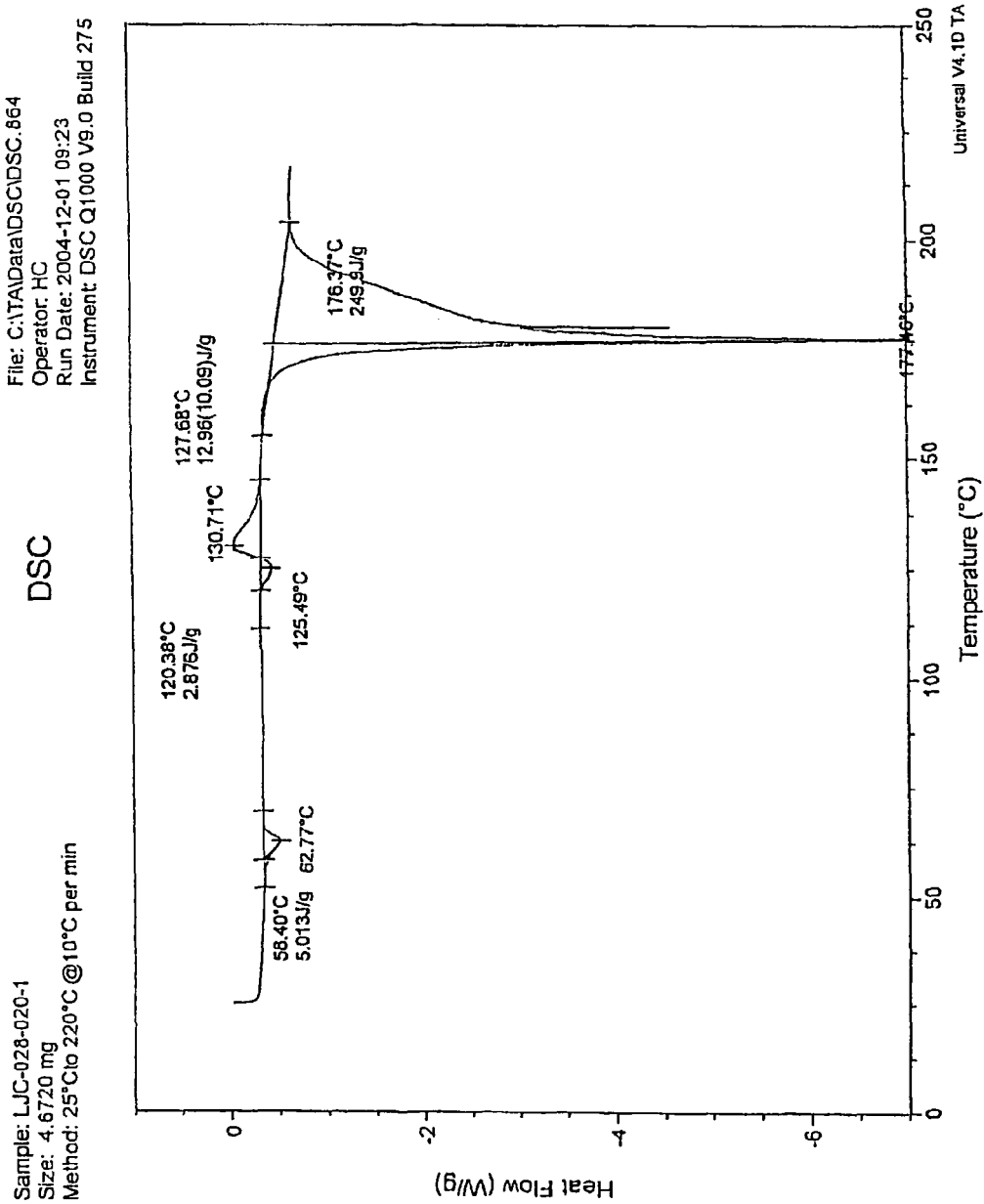
FIG. 17 shows a DSC of rotigotine 1-hydroxy-2-naphtoate

Rotigotine free base (100 mg, 3.17×10$^{-4}$ mol) was charged to a vial IPA 300 µl, 3 vol) was added at ambient. The solution was then heated to 60° C. and 1-hydroxy-2-napthoic acid (1M, 630 µl, in THF) was added and the solution held at the elevated temperature for 10 minutes. The heat was removed and the solution cooled slowly. No precipitate had formed so the solution was stored at 4° C. for 16 hours. After 10 days the solution was concentrated under vacuum to an oil which was triturated with Et$_2$O. The oil was very miscible with the Et$_2$O. The solvent was evaporated and the oil was stores at 4° C. for 5 days after which time it had crystallised. The salt was confirmed as the 1-hydroxy-2-napthoate by $^1$H NMR and confirmed to be crystalline by XRPD (FIG. 15, 16) and DSC with a peak at 176.37 (FIG. 17).

Rotigotine Hydrogen Sulphate Salt (LJC-028-007-2)

Figure 18:
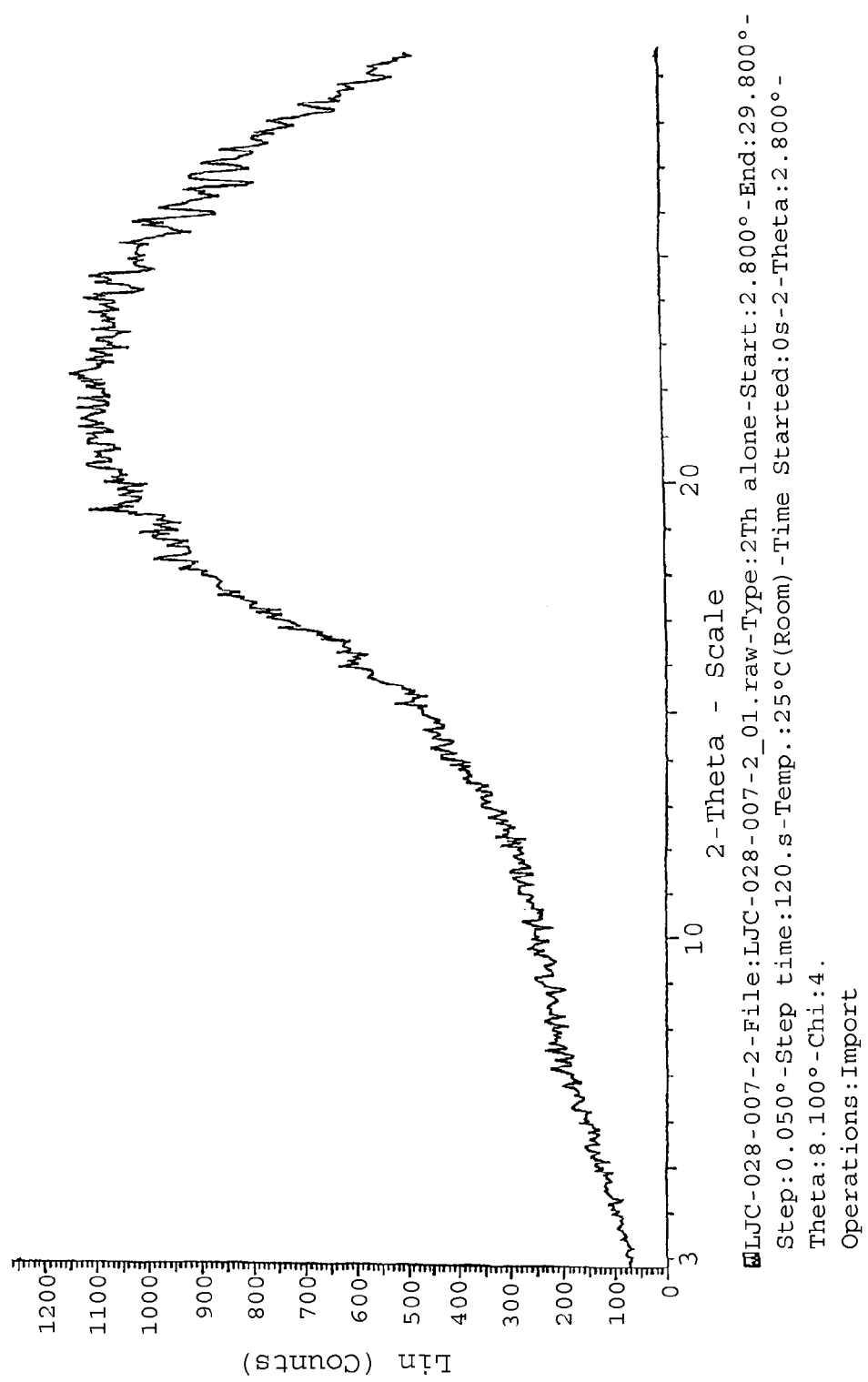
FIG. 18 shows a XRPD of rotigotine hydrogen sulphate
Figure 19:
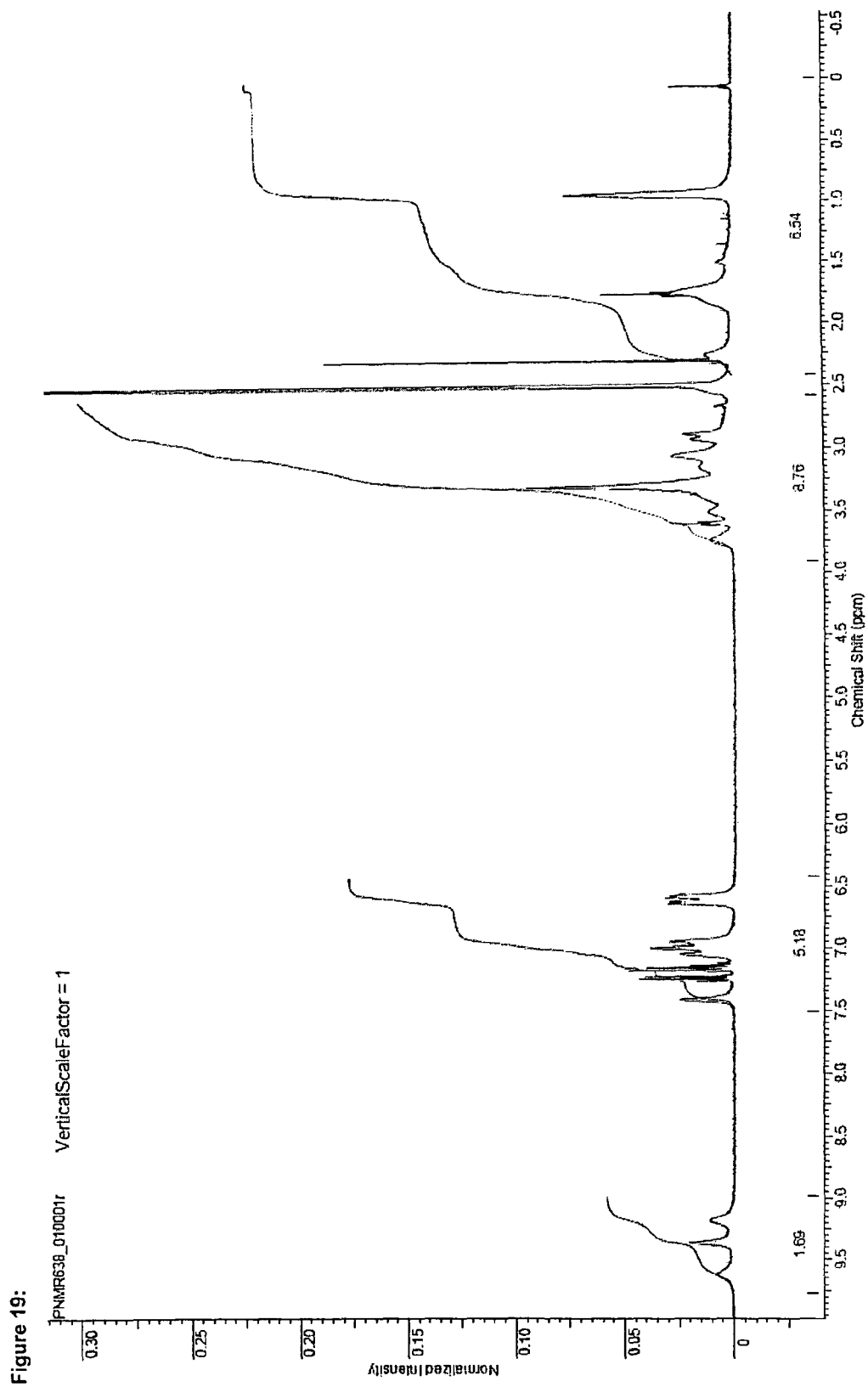
FIG. 19 shows a $^1$H NMR spectra of rotigotine hydrogen sulphate

Rotigotine free base (100 mg,) was charged to a vial as a stock solution in IPA (1 ml) and stock sulphuric acid (1 equ, 1M in THF) was added at ambient. The reaction mixture was stirred for 8 hours after which time a precipitate had formed. This was filtered, washed and dried at 40° C. under vacuum. XRPD confirmed the salt to be amorphous (FIG. 18). $^1$H NMR confirmed the salt due to significant peak shifts (FIG. 19).

Example 4

Rotigotine has both a basic and acidic group. Therefore the salt formation by using bases as well was done. Due to the high pKa value only three bases were suitable: NaOH, KOH and L-arginine (pKa=14 for hydroxides, 13.2 for L-arginine). The experimental procedures are described below.

Rotigotine Sodium Salt (LJC-028-053-1)

Figure 20:
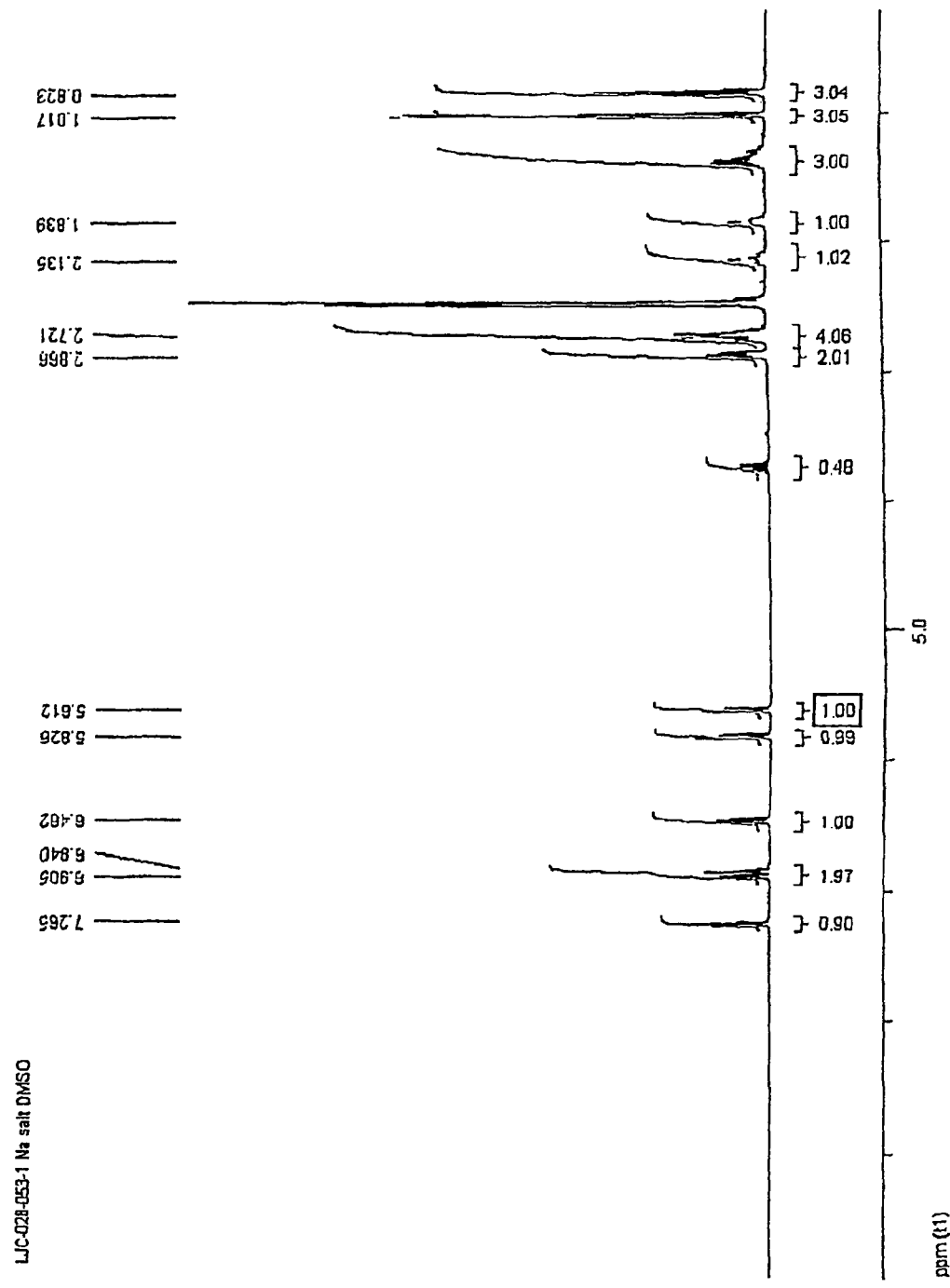
FIG. 20 shows a $^1$H NMR spectra of rotigotine sodium

NaOH (0.95M in IPA/H$_2$O, 3:1) was charged to a round bottomed flask and stirred at ambient. SPM 962 (200 mg in 600 µl) was added to the NaOH solution and an oil formed instantly. The reaction mixture was stirred at ambient for 16 hours and a pink oil was present. After a total of 72 hours at ambient the oil was concentrated under vacuum, then treated on a high vacuum line. The oil had begun to solidify after 16 hours. $^1$H NMR confirmed salt by significant peak shifts in the spectrum (FIG. 20).

Analytical Methods

Nuclear Magnetic Resonance Spectroscopy (NMR)

All spectra were collected on a Bruker AVANCE 400 MHz Spectrometer in DMSO.

X-ray Powder Diffraction (XRPD)

X-ray powder diffraction was carried out on a Bruker C2 diffractometer equipped with an XYZ stage and laser video microscope for auto-sample positioning; and a HiStar area Detector with typical collection times of 120 s. The sealed copper tube (Cu Kα radiation; 1.5406 Å) voltage and amperage were set at 40 kV and 40 mA. The X-ray optics on the C2 consists of a single Göbel mirror coupled with a pinhole collimator of 0.3 mm.

Beam divergence i.e., effective size of X-ray spot, gives a value of approximately 4 mm. Theta-theta continuous scans were employed with a sample—detector distance of 20 cm which gives an effective 2θ range of 3.2-29.8°. A corundum (α-Al$_2$O$_3$) standard (NIST 1976 flat plate) was run monthly to check the instrument calibration.

Sample preparation consisted of 1-2 mg of sample pressed lightly on a glass slide to obtain a flat surface.

Differential Scanning Calorimetry (DSC)

DSC data was collected on a TA instruments Q1000. The energy and temperature calibration standard was indium.

Samples were heated at a rate of 10° C./min, in a nitrogen atmosphere (30 mL/min purge rate) in open aluminium pans unless otherwise stated.

The invention claimed is:

1. A pharmaceutical formulation comprising at least one pharmaceutically acceptable acid addition salt of 6-(propyl-(2-thiophen-2-ylethyl)amino)tetralin-1-ol(rotigotine) and optionally a pharmaceutically acceptable electrolyte wherein said rotigotine salt has a saturation solubility in an aqueous solution which is at least 16 µmol/ml at a pH<6 and/or at least 30 µmol/ml at a pH≤5, wherein the saturation solubility is calculated based on the total amount of rotigotine in the pharmaceutically acceptable acid addition salt with the proviso that said salt is not rotigotine.HCl.

2. The pharmaceutical formulation according to claim 1, wherein the electrolyte is a chloride salt.

3. The pharmaceutical formulation according to claim 2, wherein the concentration of the chloride salt is about 1 to 140 mmol/l.

4. The pharmaceutical formulation according to claim 1, wherein the pH of the pharmaceutical formulation is ≤5.

5. The pharmaceutical formulation according to claim 1, wherein the saturation solubility in an aqueous solution is provided at about 18-25° C.

6. The pharmaceutical formulation according to claim 1, wherein the pharmaceutical formulation comprises the at least one pharmaceutically acceptable salt of rotigotine in an amount of at less than 100% of the amount necessary to achieve saturation.

7. The pharmaceutical formulation according to claim 1, wherein the at least one pharmaceutically acceptable acid addition salt of rotigotine is selected from the group consisting of dirotigotine hydrogen phosphate, rotigotine dihydrogen phosphate, rotigotine dihydrogen citrate, dirotigotine hydrogen citrate, rotigotine orotate, rotigotine 1-hydroxy-2-naphtoate, rotigotine hydrogen sulfate, rotigotine sulphate, and rotigotine hydrogen tartrate.

8. The pharmaceutical formulation according to claim 1, wherein the at least one pharmaceutically acceptable acid addition salt of rotigotine is rotigotine dihydrogen phosphate.

9. A method for treating a CNS disorder selected from the group consisting of Parkinson's disease, Restless Legs Syndrome, Parkinson Plus Syndrome, depression, fibromyalgia and Parkinson's accessory symptoms in a subject, the method comprising administering to the subject a pharmaceutical formulation comprising at least one pharmaceutically acceptable acid addition salt of 6-(propyl-(2-thiophen-2-ylethyl)amino)tetralin-1-ol(rotigotine) and optionally a pharmaceutically acceptable electrolyte wherein said rotigotine salt has a saturation solubility in an aqueous solution which is at least 16 µmol/ml at a pH<6 and/or at least 30 µmol/ml at a pH≤5, wherein the saturation solubility is calculated based on the total amount of rotigotine in the pharmaceutically acceptable acid addition salt with the proviso that said salt is not rotigotine.HCl.

10. The method according to claim 9, wherein the pharmaceutical formulation is administered to the subject by a transdermal delivery system.

11. The method according to claim 10, wherein the transdermal delivery system is an iontophoretic system.

12. The method according to claim 11, wherein the iontophoretic system comprises a device capable of delivering a current density at a level from about 0.001 to about 1.0 mA/cm$^2$.

* * * * *